(12) United States Patent
Mertens

(10) Patent No.: US 9,709,545 B2
(45) Date of Patent: Jul. 18, 2017

(54) METHODS AND APPARATUSES FOR SPECTRAL QUALIFICATION OF FUEL PROPERTIES

(71) Applicant: Tesoro Refining & Marketing Company LLC, San Antonio, TX (US)

(72) Inventor: Daniel C. Mertens, San Antonio, TX (US)

(73) Assignee: Tesoro Refining & Marketing Company LLC, San Antonio, TX (US)

(*) Notice: Subject to any disclaimer, the term of this patent is extended or adjusted under 35 U.S.C. 154(b) by 0 days.

(21) Appl. No.: 15/142,128

(22) Filed: Apr. 29, 2016

(65) Prior Publication Data

US 2017/0023538 A1 Jan. 26, 2017

Related U.S. Application Data

(60) Provisional application No. 62/196,174, filed on Jul. 23, 2015.

(51) Int. Cl.
G01N 21/31 (2006.01)
G01N 33/22 (2006.01)

(52) U.S. Cl.
CPC ............ G01N 33/22 (2013.01); G01N 21/31 (2013.01)

(58) Field of Classification Search
CPC .................................. G01N 21/31; G01N 33/22
USPC ............................................................ 356/70
See application file for complete search history.

(56) References Cited

U.S. PATENT DOCUMENTS

| | | | |
|---|---|---|---|
| 3,660,057 A | 5/1972 | Ilnyckyj | |
| 4,940,900 A | 7/1990 | Lambert | |
| 4,963,745 A | 10/1990 | Maggard | |
| 5,145,785 A | 9/1992 | Maggard et al. | |
| 5,223,714 A | 6/1993 | Maggard | |
| 5,243,546 A | 9/1993 | Maggard | |
| 5,348,645 A | 9/1994 | Maggard et al. | |
| 5,349,188 A | 9/1994 | Maggard | |
| 5,349,189 A | 9/1994 | Maggard | |
| 5,362,965 A | 11/1994 | Maggard | |
| 5,370,790 A | 12/1994 | Maggard et al. | |
| 5,452,232 A | 9/1995 | Espinosa et al. | |
| 5,475,612 A | 12/1995 | Espinosa et al. | |
| 5,490,085 A | 2/1996 | Lambert et al. | |
| 5,600,134 A | 2/1997 | Ashe et al. | |
| 5,712,481 A | 1/1998 | Welch et al. | |
| 5,712,797 A | 1/1998 | Descales et al. | |
| 5,740,073 A | 4/1998 | Bages et al. | |
| 5,763,883 A | 6/1998 | Descales et al. | |
| 5,822,058 A * | 10/1998 | Adler-Golden ...... G01N 21/359 356/300 |
| 5,858,212 A | 1/1999 | Darcy | |
| 5,861,228 A | 1/1999 | Descales et al. | |

(Continued)

OTHER PUBLICATIONS

PCT International Search Report for PCT/US11/31996 filed on Apr. 11, 2011.
PCT Written Opinion for PCT/US11/31996 filed on Apr. 11, 2011.

*Primary Examiner* — Roy M Punnoose
(74) *Attorney, Agent, or Firm* — The Pizarro Firm

(57) ABSTRACT

A method for determining property values of fuels may include using spectral data collected from one or more other fuels or fuel components. The method may include construction of spectral data representative of a fuel by weighting spectral data for another fuel and spectral data for one or more fuel components.

27 Claims, 14 Drawing Sheets

(56) References Cited

U.S. PATENT DOCUMENTS

| | | | |
|---|---|---|---|
| 6,070,128 | A | 5/2000 | Descales et al. |
| 6,140,647 | A | 10/2000 | Welch et al. |
| 6,258,987 | B1 | 7/2001 | Schmidt et al. |
| 8,017,910 | B2 | 9/2011 | Sharpe |
| 8,064,052 | B2 | 11/2011 | Feitisch et al. |
| 8,481,942 | B2 | 7/2013 | Mertens |
| 8,735,820 | B2 * | 5/2014 | Mertens ............ G01J 3/28 250/338.1 |
| 8,986,402 | B2 | 3/2015 | Kelly |
| 2004/0033617 | A1 | 2/2004 | Sonbul |
| 2004/0232050 | A1 | 11/2004 | Martin et al. |
| 2006/0162243 | A1 | 7/2006 | Wolf |
| 2007/0082407 | A1 * | 4/2007 | Little, III ............ G01N 21/359 436/139 |
| 2007/0243556 | A1 | 10/2007 | Wachs |
| 2009/0152454 | A1 | 6/2009 | Nelson et al. |
| 2009/0158824 | A1 | 6/2009 | Brown et al. |
| 2010/0131247 | A1 | 5/2010 | Carpenter et al. |

\* cited by examiner

METHODS AND APPARATUSES FOR SPECTRAL QUALIFICATION OF FUEL PROPERTIES

CROSS REFERENCE TO RELATED APPLICATIONS

This application claims priority to U.S. Provisional Patent Application 62/196,174 filed Jul. 23, 2015, which is hereby entirely incorporated herein by reference.

FIELD

The disclosed methods and apparatuses generally relate to the production and/or blending of qualified fuels and spectrographic determination of fuel properties.

BACKGROUND AND CONTEXT

Hydrocarbons, such as crude oil, may be refined to produce various products, such as jet fuel, gasoline, diesel fuel, paraffins, kerosene, naphtha, lubricating oils, asphalts, fuel oil, and liquefied petroleum gases (LPGs) such as propane and butane. Refining generally refers to a group of processes that treat, chemically change, and blend hydrocarbons. The refining process for crude oil generally breaks apart the heavier or more dense hydrocarbon chains of the crude oil at various pressures and temperatures to produce various "major cuts" or raw hydrocarbon fractions, ranging from heavy residuals to fuel oils to lighter or less dense gasoline and petroleum gas. Some refining processes may result in finished products such as diesel fuel. Other refining processes may result in intermediate products, such as fuel oil, that require further processing to produce a finished product. For example, a fuel oil may be refined further to change its chemical components in a way suitable for use in blending gasoline.

Refining methods as well as techniques for testing refinery product properties may be suitably configured to accommodate the relatively complex composition of crude oil that may be source or even batch dependent. For example, crude oil may be made up of hundreds of chemical components. Such components may include various empirical forms and isomers of chemical compounds including, for example, alkanes, aromatics, olefins, napthenes, and other compounds. The refining process may generally change the chemical make-up of crude oil in ways that may also be batch and/or process dependent. Refining processes may include, for example, distillation, coking, hydrocracking, fluidized catalytic cracking (FCC), alkylation, de-sulfurization, reforming and isomerization. Some refining processes may also rely on catalysts, such as platinum, and other process variables, such as temperature and pressure to effect conversion. Other refining processes may take a processed composition and add the processed composition together with one or more other processed compositions or fuel components without changing the underlying chemical make-up of the mixing compositions. For example, the refining process may include one or more blending operations.

During the refining process, product components may be changed in ways so as to meet a certain set of desired properties. For example, each product may have various chemical and physical properties that particularly relate to that product's usefulness. Some of those properties may be related to one or more particular components such as benzene. Other properties may be more generally related to a distribution of components in the overall fuel composition, such as specific gravity. For example, increasing octane may be useful in reducing engine "knocking" when burned, and reducing sulfur may result in lower levels of harmful sulfur dioxide, a combustion by-product. For some refining operations, a plurality of properties may change together, often in ways that are difficult to predict, thus complicating the refining process.

For some refinery products, the refining process may include one or more blending operations wherein various intermediate products and fuel components or additives are mixed to create a finished refinery product. For example, components may be added to an unfinished fuel composition to adjust properties of the composition. Generally, it may be desirable to adjust a composition's properties in a controlled manner to more efficiently lead to a useful finished fuel product. For example, adjustment of large property value shifts may be difficult or costly. Unfortunately, current methods for monitoring and estimating properties of fuels are insufficient. Accordingly, there is generally a need for improved methods of qualifying fuels or measuring fuel properties at different stages in production, and in particular for reducing property value shifts during blending operations.

Qualification of fuels is further complicated because some fuel components may be added at different stages of a product's distribution chain. For example, some components may be added to an unfinished fuel composition at a refinery where adjustment of fuel properties may be more readily accomplished. However, other components may be added at various stages along a distribution chain after leaving a refinery. For example, adding ethanol may tend to increase risk that a fuel transported in a pipeline may become contaminated such as with water. Accordingly, ethanol is typically added downstream of a refinery at a stage at which adjustment of fuel properties is more difficult. Unfortunately, optimal techniques for estimating properties of fuels prior to final addition of components are lacking. For example, current methods for estimating the properties of not-yet finished fuels may be inaccurate or highly labor intensive. Accordingly, there is generally a need for improved methods of measuring fuel properties at different stages in the production and distribution lifetime of a fuel.

SUMMARY

In some embodiments, methods for determining a property value of a fuel may include spectrographically testing a first fuel to obtain spectral data; combining the spectral data for the first fuel with spectral data for one or more fuel components to construct spectral data representative of a second fuel; and comparing the constructed spectrographic data to calibration data in order to determine a property value for the second fuel. For example, based on determined property values for a second fuel, the second fuel may be qualified as suitable for end-use or qualified as suitable for use in one or more further refining steps.

In some embodiments, methods herein may include making a second fuel from a first fuel and/or adjusting amounts and/or identities of fuel components to be added to the first fuel in order to make the second fuel with a desired or improved set of properties. Importantly, properties of more-processed fuels that may be made from less-processed fuels may be determined without needing to make the more-processed fuels or test samples of the more-processed fuels. Some embodiments herein may include modeling production of a group of more-processed fuels and selecting or grouping more-processed fuels based on desired properties.

In some embodiments, methods herein may include determining one or more property values of one or more intermediate-blended fuels that may be made during operations suitable to make a more-processed fuel from a lesser-processed fuel. For example, spectra representative of one or more intermediate-blended fuels may be constructed, and using the constructed spectra improved processes for making fuels may be identified. For example, based on constructed spectra, property values of intermediate-blended fuels may be estimated, and for example, blending steps that minimize property value shifts may be selected or chosen accordingly for use in fuel production. Accordingly, in some embodiments, a fuel may be produced more efficiently, such as in a reduced period of time, with less product waste or "give-away" and without compromising production efficiency or quality.

DETAILED DESCRIPTION

Figure 1:
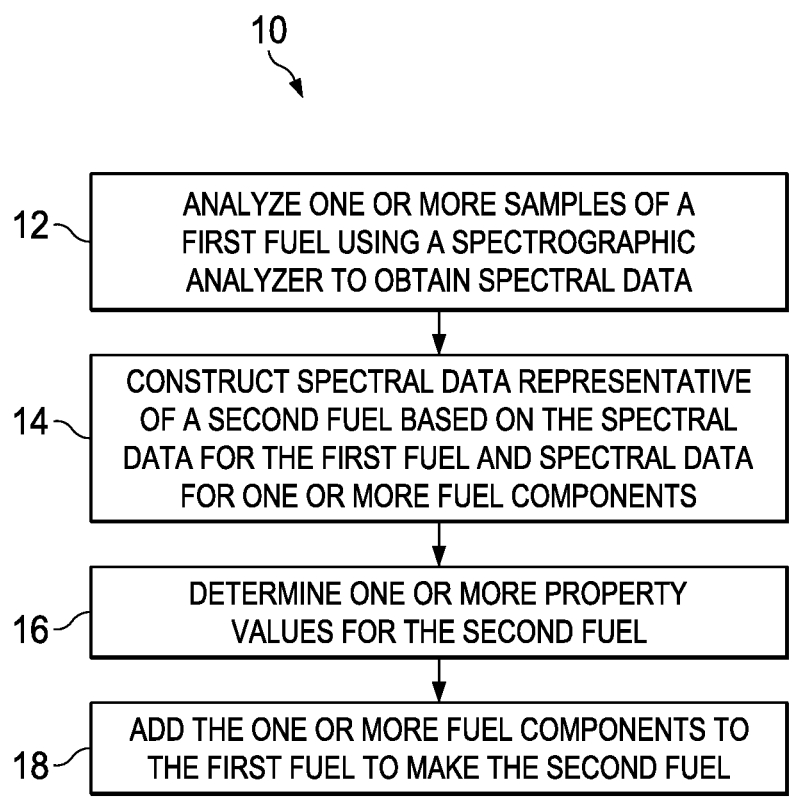
FIG. 1 illustrates embodiments of a method of deriving one or more property values of a fuel.

The following terms as used herein should be understood to have the indicated meanings.

When an item is introduced by "a" or "an," it should be understood to mean one or more of that item.

The term "alcohol-blended-product fuel" as used herein means a product fuel that includes at least one alcohol.

A "blending operation" or "blending step" as used herein refers to a step in refinery processing in which two or more compositions are mixed to produce another composition under conditions wherein covalent changes during mixing are minimal. For example, during a refinery blending operation, two or more fuel compositions may be combined under conditions (e.g., temperature, pressure, and/or catalytic activity) wherein covalent conversion of molecular species therein to other molecular species is minimal.

The term "blendstock" as used herein refers to a composition derived from a source of crude oil which has been processed using one or more refining operations to prepare the composition for blending with other fuel components. A blendstock may be processed such that it may be used in one or more blending steps with other fuel components to make a product fuel. Blendstocks, include, by way of example, reformate and alkylate fuels.

The term "fuel component" as used herein means a composition that may be included in a fuel. Some fuel components may be substantially purified compounds or additives, such as certain ethers and purified alcohols. For example, ethanol is a common fuel component that may be added to a fuel in the form of denatured ethanol which generally includes ethanol at greater than about 95% purity by volume. Other fuel components may be more complex mixtures of chemical compounds, including for example, various blendstocks and other intermediate compositions which may be derived from crude oil. For example, a straight-run naphtha distillate is a common fuel component that may be made from crude oil. Straight-run naphtha may, for example, include a combination of hydrocarbons predominantly within a range of 6 carbon atoms to about 12 carbon atoms per hydrocarbon molecule, and may be characterized by a boiling range of between about 65° C. to about 230° C.

The term "intermediate fuel" as used herein means a composition to which one or more fuel components may be added during refinery processing. In refinery processing, one or more fuel components may be added to an intermediate fuel to produce, for example, another intermediate fuel, a product fuel, or a sub-grade fuel. An intermediate-blended fuel may be a composition that is readily isolatable in a certain blending protocol or that may exist only transiently in a certain blending protocol.

The term "product fuel" as used herein means a fuel configured for end use by a consumer. A product fuel may also be referred to as a finished-product fuel or finished fuel.

The term "qualified fuel" as used herein means a fuel that has been determined to meet one or more property values. For example, qualified fuels that are product fuels may be determined to meet a set of product specifications and environmental standards to establish that the product fuel is configured for sale and use in one or more localities.

The term "sub-grade fuel" as used herein means a composition to which one or more fuel components may be blended to make a product fuel. A sub-grade fuel may be configured for transport from a refinery to a distribution terminal. For example, a sub-grade fuel may be a substantially alcohol-free fuel not yet in a form ready for end use and may include non-alcoholic components of an alcohol-blended-product fuel. Addition of alcohol to the sub-grade fuel may make the alcohol-blended product fuel. Components added to a sub-grade fuel to form a product fuel may be absent in the sub-grade fuel or may be present in the sub-grade fuel at reduced concentrations as compared to final concentrations intended in the product fuel.

Methods are described herein for determining property values of fuels using spectral data collected from one or more other compositions. For example, a sub-grade fuel may be tested in order to determine values of different properties of a product fuel which may be made from the sub-grade fuel by addition of one or more fuel components. In some embodiments, a property value of a fuel may be determined without ever needing to test the fuel itself. For example, an alcohol-free-sub-grade fuel may be blended with an alcohol, such as ethanol, to create an alcohol-blended-product fuel, and the alcohol-blended-product fuel may be qualified based on spectral analysis of the alcohol-free-sub-grade fuel. In some embodiments, a sub-grade fuel may be spectrographically tested at a refinery to produce spectral data, the spectral data may be conditioned to determine property values of a product fuel, the sub-grade fuel may be transported from the refinery to a distribution facility, additional fuel components may be mixed to make the product fuel, and then the product fuel may be shipped to a retail supplier.

In some embodiments, a sub-grade fuel that is substantially free of alcohol may be made at a refinery. Or, a refinery may create a sub-grade fuel that includes alcohol in an amount below an amount intended for end use. Advantageously, those sub-grade fuels may be transported without alcohol or with only trace or limited amounts of alcohol present. For example, a sub-grade fuel may be transported between a refinery and distribution facility using a pipe line. The sub-grade fuel may be transported therein without fuel components that might attract undesirable materials or debris that would pose a significant contamination risk if the finished product fuel itself was transported. For example, fuels containing alcohols may be particularly prone to contamination because they may tend to accumulate undesirable levels of water. Other contaminants may likewise collect in a fuel containing alcohol including contaminants with an affinity for hydrophilic components of a fuel. In some methods herein, those problems may be eliminated or reduced by adding alcohol to a sub-grade fuel at a stage downstream of a refinery, such as at a distribution terminal during discharge into a fuel tanker truck for transport to a retail fuel station. Moreover, the sub-grade fuel may be transported from the refinery with high confidence that a finished-product fuel made from the sub-grade fuel will meet product specifications.

In some embodiments, an intermediate or blendstock fuel may be spectrographically tested in order to determine properties of other fuels that may be made during blending operations in the refining process. For example, a blendstock fuel, such as an alkylate or reformate fuel, may be blended with other fuel components in one or more blending operations to make a sub-grade fuel ready for transport from a refinery, a product fuel, or another blended composition. More generally, in some methods herein, fuels for which blending is complete and/or intermediate fuels that may be subject to further blending operations may be qualified based on spectrographic testing of one or more pre-blended fuel components.

In refinery blending, one or more fuel components may often be blended with a less-processed fuel to make a more-processed fuel. For example, blending operations may produce a blended and more-processed fuel that is of higher commercial value than the pre-blended components from which it was made because the blended fuel may possess properties that are better suited for a fuel's end use. A fuel may be considered a more-processed fuel with respect to a less-processed fuel because the cost and effort to make a product fuel from the more-processed fuel is reduced as compared to that for the less-processed fuel. For example, a more-processed fuel may be further along in refinery processing to make a product fuel than a less-processed fuel. In some embodiments herein, one or more property values of a more-processed fuel may be determined by spectrographically testing a less-processed fuel. Importantly, property values may be calculated without needing to make the more-processed fuel or a test sample of the more-processed fuel. Furthermore, property values may be determined or modeled in one or more intermediate compositions, including, for example, those that may exist transiently or in an isolatable form, that may be used in processing to make the more-processed fuel.

For example, in some embodiments, a value of a fuel property may be calculated following one or more blending operations in a series of blending operations. Generally, unless the context dictates otherwise, where it is described that a fuel property value may be calculated, values for any number of other fuel properties may also be calculated. Property values may sometimes be calculated and compared to one or more property value thresholds. Therefore, one may determine, in a series of blending operations, whether any step in the series may produce a fuel with a property value that may meet, exceed, or fall below a property value threshold. In addition, one may determine other characteristics of properties as they may change throughout a series of blending operations. For example, included among characteristics of one or more properties that may be calculated in a series of blending operations are overall change in one or more property values, one or more difference values for one or more property values (e.g., between adjacent or other blending operations in a series), interactions of one or more properties with one or more other tracked properties, other characteristics, and combinations thereof.

In some embodiments, a value of a fuel property may be calculated throughout more than one series of blending operations. For example, in different hypothetical series of blending operations or blending scenarios, the identities, amounts, or order of fuel components that may be added to one or more less-processed fuels may be varied. Upon determining property values for fuels made in different blending scenarios, one may select a scenario based on one or more desired characteristics of the determined fuel property values. For example, one may choose a series of blending operations where overall property value shifts or property value shifts between adjacent or critical operations in the series is minimized or controlled. Therefore, a particular blending scenario may be selected from among a group of blending scenarios to achieve more efficient fuel production. For example, unexpected swings in property values that sometimes may occur in fuel production may be modeled. Accordingly, problems may be anticipated and actions taken to appropriately correct the problem before fuel creation. Accordingly, creation of fuels possessing property values that had unexpectedly changed beyond acceptable bounds, which may involve a situation where undesirable addition of fuel components to counteract those changes might be needed, may be avoided. Avoiding such corrections may amount to a considerable cost savings.

In some embodiments, a material cost may be associated with one or more fuel components that may be added to a fuel as part of a modeled blending scenario. For example, the cost of fuel components, including, for example, substantially purified compounds or blendstocks, may be known based on current market conditions or other criteria. Other criteria that may be associated with a material cost of a fuel component including, for example, current stock levels, changing market conditions, transport cost for obtaining a component or precursor(s) of a component, refining costs for making a component from one or more precursors, risk of supply chain interruptions, and/or other criteria may also be considered. Criteria associated with a material cost of a fuel component may be updated regularly or as needed at any convenient interval. In some embodiments, a material cost estimate may be determined or determined along with a calculation of property values for one or more blending operations or for more than one blending scenario. Other components of the total cost of executing a blending scenario such as labor costs may also be calculated.

In some embodiments, an overall material cost for making one or more more-processed fuels from one or more less-processed fuels may be determined. Or, an overall material cost may be calculated for each member of a group of more-processed fuels. For example, in some embodiments, a group of more-processed fuels may be defined based on different blending scenarios including addition of various fuel components or component amounts to one or more lesser-processed fuels. Groups of more-processed fuels may be organized based on various criteria. For example, a group of more-processed fuels may be created wherein each member of the group is suitably qualified for an intended purpose (e.g., a product fuel may be qualified as meeting specifications for end-use or a fuel at another stage of production may meet other specifications). Or, a group of more-processed fuels may be created wherein each member of the group is suitably qualified for the fuel's intended purpose and wherein property value shifts associated with making the member fuel meet one or more desired criteria. One may then examine a group of fuels together with cost estimates for making the fuels and select a desired fuel for creation. More generally, in the methods described herein, the results of different blending scenarios or production scenarios may be organized, and one may select a blending or production scenario that produces a fuel associated with one or more desired attributes. For example, a fuel may be selected based on attributes of the fuel or characteristics of making the fuel including, for example, cost of making the fuel, time for making the fuel, optimum process latitude with respect to one or more fuel property values, minimized property value shifts, minimized risk of corrective blending operations, other attributes and combinations thereof.

In some embodiments, a refinery may qualify a product or other fuel by collecting spectral data from another fuel that may be used to make that product or other fuel, and the collected spectral data may then be conditioned so that it may be compared to calibration data suitable to correlate one or more primary or non-spectrographic properties of the product or other fuel to the conditioned spectral data. To condition spectral data, a process of spectral construction may be executed. For example, absorption data may be determined for a first fuel lacking certain fuel components specified in a second fuel to be qualified. Data collected from the first fuel may be conditioned so that resulting constructed absorption data is representative of spectral data collected from the second fuel as if the lacking components were already present.

Some of the advantages herein may be explained in an exemplary manner by considering qualification of an alcohol-blended-product fuel based on an alcohol-free-sub-grade fuel (or other sub-grade fuel including reduced amounts of alcohol as compared to an amount specified for an alcohol-blended-product-fuel). By testing the sub-grade fuel (e.g., before addition of alcohol to its specified final concentration) to obtain spectral data, and conditioning the spectral data by constructing spectral data representative of the intended alcohol-blended-product fuel, a refinery may qualify product fuels with significant cost savings over other methods. For example, those other methods may qualify an alcohol-blended-product fuel by physically adding alcohol to a sample of a sub-grade fuel and collecting spectral data for the now blended product-fuel sample. Physical addition of an appropriate amount of alcohol to a sample may be mechanically intensive particularly where multiple samples need to be made. Expenditures of time dedicated towards mechanical addition of alcohol to samples of a fuel may be lessened by modifying an analyzer to include in-line analysis capabilities. However, while addition of alcohol to a sample of fuel may be accomplished with an in-line analyzer, modification of analyzers in this way increases equipment cost and may increase demands on analyzer maintenance. Moreover, equipment-specific calibrations may need to be adjusted for an in-line analyzer, and correlation of different equipment, some of which may be configured with an in-line analyzer, may be difficult. Furthermore, to determine property values for addition of different components and/or different amounts of fuel components, distinct calibration curves and multiple sample preparations may be needed which may be a time intensive procedure.

In contrast, with methods disclosed herein, sample preparation may be significantly reduced. Furthermore, spectra representative of fuels produced by addition of various amounts of one or more added fuel components may be constructed without the need to prepare multiple samples and without incurring associated demands on labor. In some embodiments, including, for example, embodiments described above with respect to modeling of different blending scenarios, where a plurality of spectral data may be constructed, the spectral data may be used to optimize protocols for fuel creation. For example, because property values for multiple product fuels may be readily determined, optimized compositions may be selected and products may be created that minimize product give-away or that are optimized based on other criteria. Therefore, included among advantages of certain embodiments of methods and apparatuses herein are increased precision or accuracy, minimized sample preparation, reduced cost for qualification and equipment maintenance, increased accuracy of sharing data between equipment, and creation of optimized products such as those that minimize product give-away, which may occur when an unnecessary quantity of a component, coarsely estimated so as to achieve a certain property value, is added in order to attempt to meet a product specification. In addition, methods herein may be automated and may be particularly amenable for use in apparatuses configured for spectrographic in-line process monitoring. For example, a blending unit may be configured with instrumentation suitable to sample and test a fuel during blending operations which may be used to track changes in property value at regular or continuous intervals during blending operations.

In some embodiments, methods herein may include comparing constructed spectral data to calibration data, including standard calibration data and/or global calibration data. For example, in some embodiments, a spectrometer may be a globally-calibrated spectrometer, and methods herein may include comparing constructed spectral data to global-calibration data using one or more globally-calibrated spectrometers. Accordingly, methods herein may be integrated with direct-match spectrographic methods as further described in U.S. Pat. Nos. 8,481,942 and 8,735,820, commonly owned by Applicant, the disclosure of each of which is wholly incorporated herein by reference.

In some embodiments, calibration data suitable to correlate primary or non-spectrographic properties to spectral data may be collected by spectrographically analyzing one or more suitable reference fuels. For example, a reference fuel may be chemically similar to a product fuel or other fuel (e.g., a sub-grade fuel, intermediate fuel or other fuel) for which knowledge of property values is desired. In some embodiments, chemical similarity of two or more fuels may be established based on commonalities of source, type, and/or processing between the two or more fuels. In some embodiments, chemical similarity may also be established or corroborated based on other chemical testing methods and/or criteria. For example, various techniques and metrics for using, generating, and evaluating or selecting calibration data, including methods for determining levels of chemical similarity, are further described in the references incorporated herein. For example, in some embodiments, as described in U.S. Pat. No. 8,735,820, calibration data may be selected from a spectral library including data associated with one or more reference fuels.

In some embodiments, calibration data may be stored and later used without needing to retest the reference fuels used to create the calibration data. For example, a reference fuel may be analyzed in one or more spectrographic analyzers to derive calibration data that is then stored in one or more reference databases. When a new batch of fuel is formed, an analyzer may access the calibration data for use in qualification of the new batch. Spectrographic analyzers, or spectrometers, may include, for example, those associated with the following wavelengths or techniques: Near Infrared (NIR), Mid Infrared (MIR), Near and Mid (full range) Infrared (IR), Fourier Transform Near Infrared (FTNIR), Fourier Transform Mid Infrared (FTMIR), Fourier Transform Near and Mid (full range) Infrared (FTIR), Nuclear Magnetic Resonance (NMR) and Raman. Analyzers suitable for use in methods herein include those associated with infrared spectroscopy. For example, in some embodiments herein, absorption spectroscopy may include analysis of bands between about 1500 $cm^{-1}$ and 5200 $cm^{-1}$. In some embodiments, Raman spectroscopy may be used together with or as an alternative to absorption infrared spectroscopy. In some embodiments, where Raman spectroscopic methods may be applied, inelastically-scattered light characterized by a spectral shift of between about 200 $cm^{-1}$ to 1600 $cm^{-1}$ may be collected. By way of nonlimiting example, such analyzers may be stand-alone instruments suitable for batch testing, such as those produced by ABB Bomem and by Analect, or may be on-line instruments (i.e., connected to fuel production equipment) suitable for in-stream testing, such as those produced by ABB Bomem, and Analect. Such analyzers may be implemented in hardware and/or software or a combination of hardware and software.

A refinery may use calibration data to calibrate a spectrographic analyzer to product properties. For example, properties of fuels may include, but are not limited to, those shown in Table 1:

TABLE 1

| Property | Spark Ignition fuel (e.g. Gasoline) | Turbine Fuel (e.g. Jet) | Compression Ignition Fuel (e.g. Diesel) | Distillate Fuels (e.g. Htr Oil) |
|---|---|---|---|---|
| RON | x | | | |
| MON | x | | | |
| RVP | x | | | |
| $T_{v/l-20}$ | x | | | |
| Specific Gravity | x | x | x | x |
| Aromatics | x | x | x | |
| Polynuclear Aromatics | | | x | |
| Olefins | x | | | |
| Benzene | x | | | |
| Oxygen | x | | | |
| Ethanol | x | | | |
| Distillation | x | x | x | x |
| Flash | | x | x | x |
| Viscosity | | x | x | x |
| Analine Point | | x | | |
| Cetane Number | | | x | |

"RON" refers to Research Octane Number. "MON" refers to Motor Octane Number. "RVP" refers to Reid Vapor Pressure. $T_{(v/l)}=20$ refers to the temperature at which the vapor to liquid ratio equals 20. Distillation properties may be obtained with respect to IBP, T10, T30, T50, T70, T90, EP, E200 and E300, for example.

In some embodiments, to generate calibration data, and/or calibrate a spectrometer to a product's properties and property values, a refinery may take samples of reference fuel, and send a first portion of each sample to a laboratory for primary (non-spectrographic) testing, e.g., engine testing, according to ASTM standards, such as ASTM D2700 used for testing motor octane number (MON) of spark-ignition engine fuels. The refinery may run a second portion of each sample through a spectrographic analyzer to generate spectral data, and compare the primary test data to the spectral data in order to correlate product properties and property values to the spectral data. For example, a refinery may determine the relationship between an engine test MON value of a sample against that sample's wavelength-dependent absorption data. In general, each comparison may generate calibration data. A refinery may aggregate data together and use statistical tools to generate calibration data and/or to calibrate a spectrographic analyzer to specific product property values. For example, a refinery may use a multivariate regression analysis, such as that specified in ASTM E1655, to develop a calibration model, curve, or function from the calibration data. After calibration, a refinery may use the spectrographic analyzer to analyze the properties of a fuel sample and predict property values without having to also analyze the sample using primary or non-spectrographic testing. For example, a product fuel may be blended and a sample of that fuel taken for analysis to produce spectral data that is compared to calibration data to determine property values. Alternatively, a sample of one fuel, such as a sub-grade fuel, may be spectrographically tested and the collected spectrographic data conditioned using a process of spectral construction. The constructed spectral data may then be compared to calibration data to derive property values of another fuel, such as a product fuel, that may be made from the sub-grade fuel.

FIG. 1 illustrates exemplary embodiments of a method 10 for qualifying a fuel or making a qualified fuel (referred to as a second fuel in method 10) based on spectral data collected from a first fuel and including a process of spectral construction. In a step 12, one or more samples of the first fuel may be collected and spectrographically analyzed to obtain spectral data. In a conditioning step 14, the spectral data collected for the first fuel may be combined with spectral data for one or more fuel components in a process to construct spectral data representative of the second fuel. For example, spectral data for the first fuel may be combined with spectral data for one or more fuel components that may be added to the first fuel to make the second fuel. In a step 16, one or more property values for the second fuel may be determined from the constructed spectral data. In some embodiments, methods herein may further include making the second fuel or deciding whether or how to make a fuel based on the one or more determined property values. For example, as shown in step 18, a step that may, in some embodiments, be selectively executed if one or more property values are within specification limits, one or more fuel components may be added to the first fuel in amounts suitable to make the second fuel.

In some embodiments, the spectrographic analysis executed in the step 12 may include collection of absorption data in an infrared region of the spectrum, such as the NIR, the MIR, or the full IR range, and may use an instrument, such as, for example, an FTIR spectrometer. In some embodiments, one or more spectrometers configured to measure levels of Raman scattering may also be employed. Collection of spectral data may, for example, include measurement of a sample representative of a certain batch of a first fuel such as a blendstock fuel, sub-grade fuel, or intermediate fuel. Other blank and/or appropriate samples may also be analyzed together with one or more fuel samples. Particular blanks analyzed may depend upon specific laboratory protocols and tool configurations. In some embodiments, spectral information, such as tool specific calibrations and/or spectra of sample cells, dilution solvents, or other blanks, useful to convert a raw signal to sample absorption data may be internally stored in tool software.

In the conditioning step 14, spectral data may be constructed that is representative of a second fuel. In some embodiments, the second fuel may be a fuel that may be made from the first fuel by addition of an amount of one or more fuel components. In some embodiments, the one or more fuel components may be predetermined fuel components that may be added in predetermined amounts to the first fuel to make the second fuel.

Construction of second fuel spectral data (step 14) may include combining spectral data collected in step 12 for the first fuel and fuel component spectral data. As part of step 14, spectral fuel data for the one or more fuel components may be collected and/or accessed. For example, absorbance data representative of one or more fuel components may be stored in a database and may be accessed for use during spectral data construction. Alternatively, physical samples for one or more fuel components may be measured to obtain fuel component spectral data. For example, in some embodiments, a fuel component may be a blendstock, and spectral data for the blendstock component may sometimes be obtained by collecting and measuring one or more samples of the blendstock. Spectral data for other components, including, for example, additives such as certain alcohols and ethers, may be accessed from a spectral database.

In some embodiments, construction of spectral data representative of a second fuel (step 14) may include use of Equation 1 to estimate the absorbance of a second fuel at a given wavelength ($\lambda$) or within a certain spectral band from absorbance data collected for the first fuel and absorbance data for fuel components.

$$\text{Abs.(Second fuel)}(\lambda) = (x_1)\text{Abs.(First fuel)}(\lambda) + (x_2)\text{Abs.(Component 1)}(\lambda) + \ldots (x_n)\text{Abs.(Component } N)(\lambda) \quad \text{(Equation 1)}$$

In some embodiments, scattered light intensity or other suitable forms of spectroscopic data may also be employed to construct spectral data representative of a second fuel in step 14. For example, scattered light intensity or other forms of spectroscopic data may be substituted for absorbance data in Equation 1 and in other appropriate equations herein. In Equation 1, weighting factors ($x_1, x_2, \ldots, x_n$) may modify the relative contributions of absorbance data from the first fuel and absorbance data from the one or more fuel components. In some embodiments, weighting factors may be determined based on relative amounts of fuel components as they may be included in the second fuel. For example, in some embodiments, if an amount of an added fuel component is predetermined, a corresponding weighting factor may be determined based on the relative amount of the component set for inclusion in the second fuel. Relative amounts of fuel components may be expressed as volume fractions, weight fractions or the amounts may be expressed in other suitable ways. For example, as shown in Equation 2, the weighting factor ($x_1$) used to adjust absorbance data derived from the first fuel may be related to the volume of that first fuel incorporated in the second fuel and the total volume of the second fuel. As also shown in Equation 2, the weighting factor ($x_1$) may also be expressed in terms of the volume (or other suitable metric related to amount) of the first fuel incorporated in the second fuel and volumes of fuel components that may be added to make the second fuel:

$$x_1 = \text{(Weighting factor for first fuel)} = \text{[Volume of first fuel]/[Total volume of second fuel]} = \text{[Volume of first fuel]/[(Volume of first fuel)+(Volume Component 1)+ \ldots (Volume Component } N)] \quad \text{(Equation 2)}$$

In some embodiments, as shown in Equation 3, to account for matrix effects, which may be small for some compositions, a wavelength dependent correction factor $j(\lambda)$ may be used in construction of spectral data representative of a second fuel (step 14).

$$\text{Abs.(Second fuel)}(\lambda) = (x_1)\text{Abs.(First fuel)}(\lambda) + (x_2)\text{Abs.(Component 1)}(\lambda) + \ldots (x_n)\text{Abs.(Component } N)(\lambda) + j(\lambda) \quad \text{(Equation 3)}$$

As further described herein, correction factors $j(\lambda)$ may, in some embodiments, be determined from constructed spectral data and spectral data collected from physically-blended reference fuel samples. For example, physically-blended-reference-fuel samples may include samples of blended-product fuels that are tested during initial setup of methods described herein.

More generally, physically-blended-reference-fuel samples may be chemically similar to the fuel for which property values are determined. Chemical similarity may be established or verified using similar metrics and techniques as may be used for some other reference samples described herein, such as, particularly, those that relate primary or non-spectrographic properties to spectral data. In some embodiments, as shown in Equation 3, a single correction factor $j(\lambda)$ may be applied. However, in some embodiments, particularly where more than one fuel component may be added to a first fuel, individual correction factors may be applied for each of the one or more fuel components. In some embodiments, it may be determined that some fuel components may interact nonlinearly with other fuel components included in a second fuel whereas other fuel components are substantially matrix independent or matrix effects may be negligible over certain ranges of fuel component addition, and correction factors may be included only for those fuel components that exhibit significant matrix effects.

In the step 16, one or more property values of a second fuel may be determined using the spectral data constructed in step 14. To calculate property values of the second fuel using constructed spectral data, calibration data relating non-spectrographic properties to spectral data may be used. For example, as described above, a refinery may generate primary test data and spectral data for reference samples and use that data to generate one or more correlation models, curves, or functions. Once a correlation is generated, spectral data and/or constructed spectral data of the second fuel may be related to property values using the correlation and property values accordingly determined. In some embodiments, to determine a property value of the second fuel, one or more absorbance values for constructed spectral data may be compared to calibration data. In some embodiments, calibration data may be collected for reference product standards and the information stored in computer memory and used as needed. Alternatively, reference product standards may be appropriately stored and re-tested as needed to verify calibration data or generate new calibration data. Generally, calibration data may include data suitable to correlate spectral data, including absorbance data, to property values of the second fuel. For example, representative property values of some fuels that may be compatible with methods herein are shown in Table 1. In some embodiments, any of the various properties indicated therein in Table 1 or other suitable property values of fuels may be determined.

In some embodiments, the steps 12-16 of the method 10 may be executed in a method of determining one or more property values of a fuel. In some embodiments, methods herein may further include making the fuel for which property values have been determined. For example, if the second fuel suitably meets one or more determined property values, the second fuel may be made such as by adding one or more fuel components as indicated in the step 18. In some embodiments, the first fuel may be an intermediate fuel or blendstock fuel and addition of fuel components may produce a second fuel including any of a more-processed intermediate fuel, a sub-grade fuel which may be ready for transport from a refinery, or a product fuel. Accordingly, in some embodiments, a second fuel may be made prior to transport from a refinery. For example, the first fuel may be a sub-grade fuel and the second fuel may be a finished-product fuel that may be made downstream of the refinery. In some embodiments, constructed spectral data may include spectral data representative of more than one fuel components, and when making the fuel (e.g., for which the constructed spectral data is representative) it may be convenient to add one or more of the fuel components before the first fuel exits a refinery whereas it may be preferable to add one or more other fuel components downstream of the refinery. Based on property values as determined in the step 16, confidence that the first fuel may be transported from the refinery and that downstream addition of other fuel components (step 18) may produce a useful fuel product meeting specification may be high. In some situations, including, for example, if the property values determined in step 16 are deemed unacceptable, corrective actions may be taken before a fuel leaves a refinery. For example, one or more additional fuel components may be added to a fuel in order to adjust unacceptable property values to achieve acceptable property values.

In some embodiments, in the step 18, more than one fuel component may be added, and it may be desirable or necessary based on available equipment to add at least some of the fuel components or some amount of one or more fuel component consecutively in more than one blending operation. Importantly, with some of the methods disclosed herein, property values may be determined for either or both of intermediate-blended fuels and/or final-blended products. Property values of intermediate-blended fuels may be determined before some or all additions in a certain blending step or process are made. For example, with reference back to step 14, in some embodiments, constructed spectral data may be representative of an intermediate-blended fuel made by adding only some components or some amounts of some components intended for addition to make the second fuel. Spectra for various intermediate-blended fuels may be constructed and used to determine property values for various intermediate-blended fuels. Therefore, property value shifts and/or swings may be calculated for any number of intermediate-blended fuels. Generally, property value swings may refer to undesirable shifts in a property value between one or more steps in a refinery process, including changes in a property value wherein a value may change in one or more steps in ways that may demand property value correction. In some embodiments, one may determine if one or more intermediate-blended fuels possess a property value that is below a minimum property value threshold, exceeds a maximum property value threshold, or is outside of a desired property value range.

In some embodiments, one or more samples of an intermediate-blended fuel may be physically collected and tested. Selection of intermediate-blended fuel samples for testing may sometimes be based on estimated property values of an intermediate-blended fuel based on testing of one or more less-processed fuels. For example, in some embodiments, intermediate-blended fuels may be identified that exhibit property value shifts that are more than desired when the composition is made in a given blending process. For example, by examining property values throughout several blending operations, one or more intermediate-blended fuels may be identified for which it may be desirable to collect and test physical samples when the one or more intermediate-blended fuels are made. Moreover, in some embodiments, an added amount of one or more fuel components may be calculated for which a certain property value may shift beyond an ideal or stable level. Accordingly, with methods described herein, intermediate stage blending operations where property shifts are expected may be identified and corrected before a given property changes beyond an acceptable or desired level.

Figure 2A:
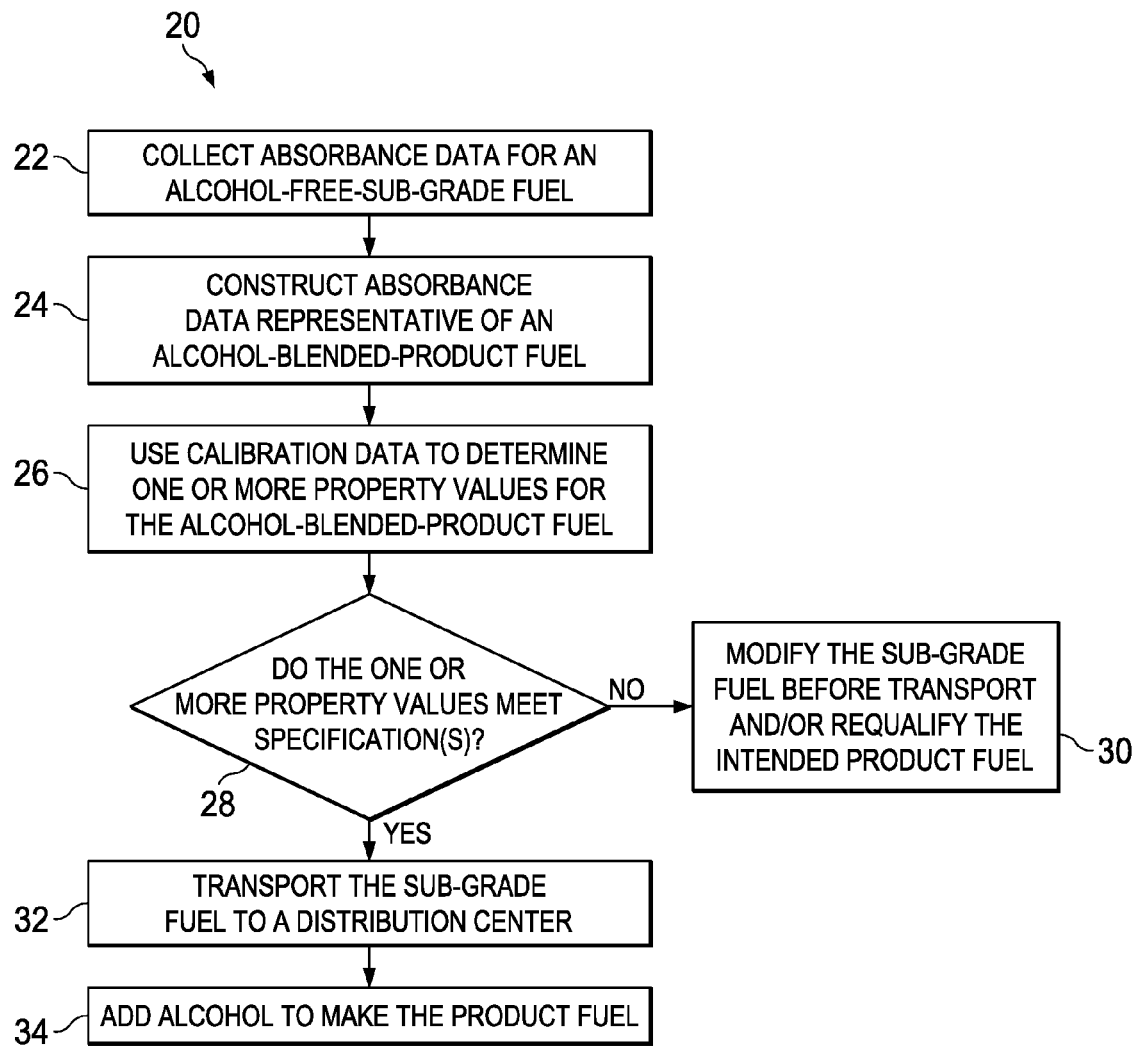
FIG. 2A illustrates embodiments of a method of deriving one or more property values of an alcohol-blended-product fuel.
Figure 2B:
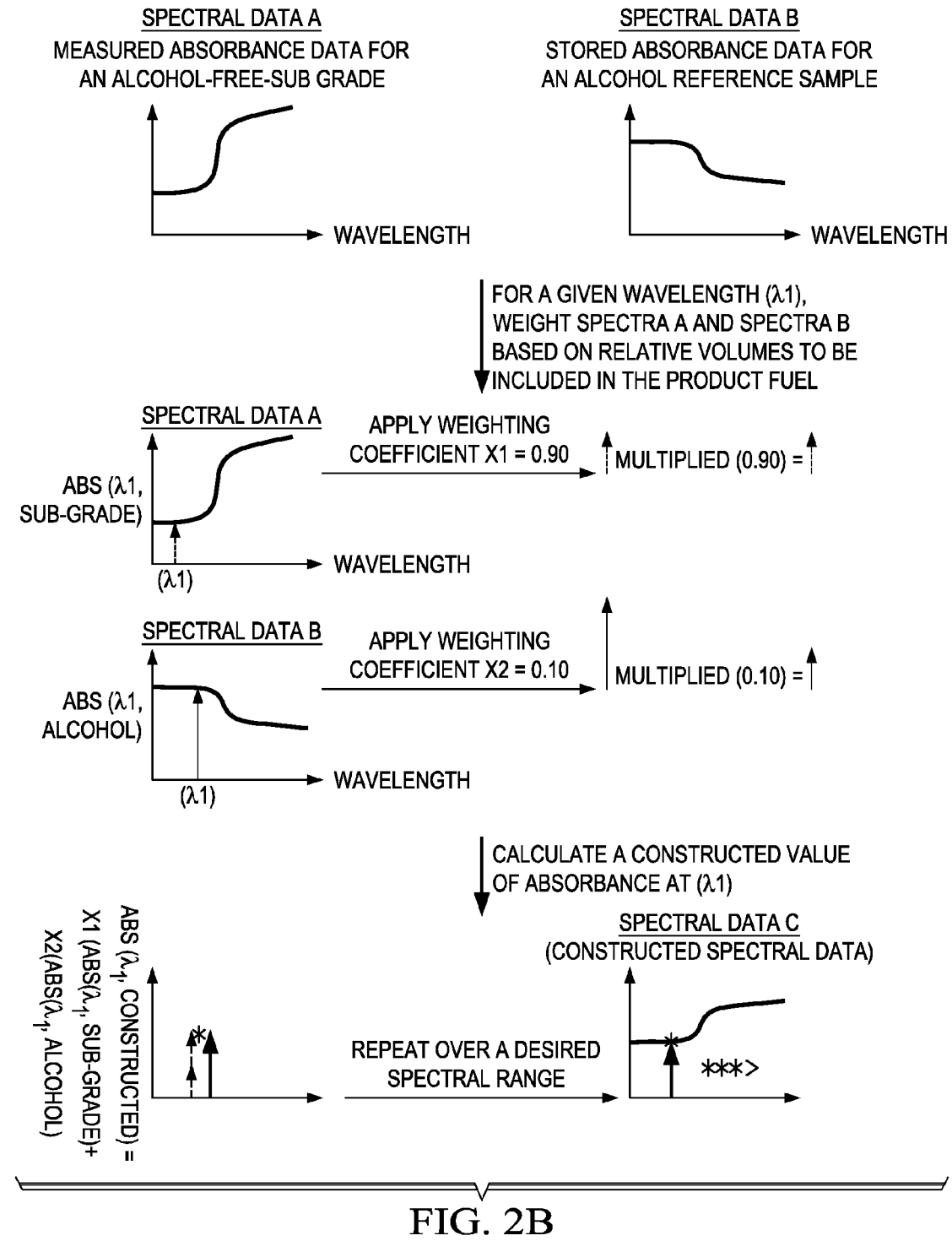
FIG. 2B illustrates embodiments of methods for constructing spectral data.
Figure 2C:
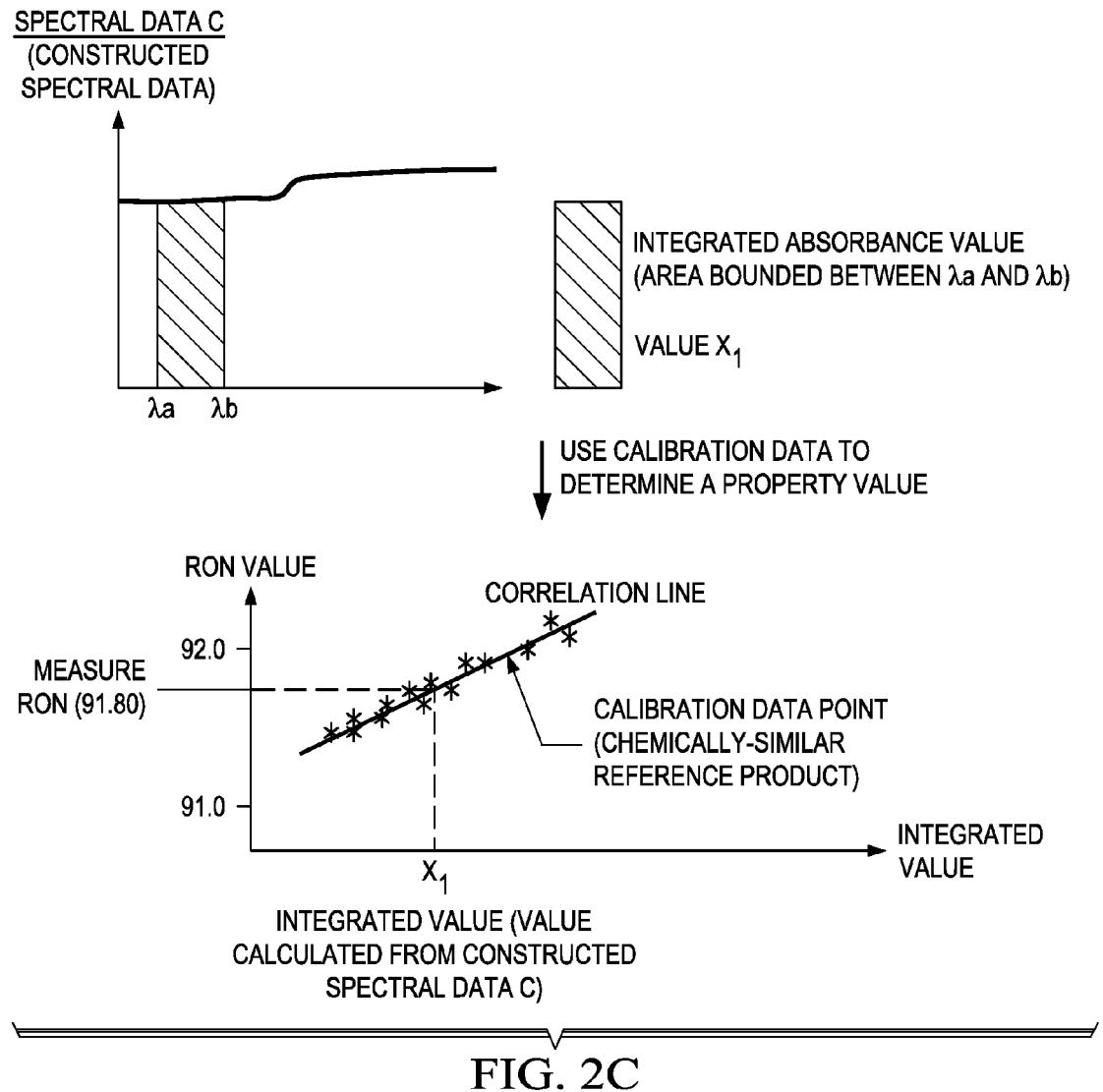
FIG. 2C illustrates embodiments of methods for determining a property value from calibration data and constructed spectral data.

Methods herein are also described in relation to FIGS. 2A, 2B, and 2C. FIG. 2A illustrates method 20 which includes embodiments wherein a second fuel is an alcohol-blended-product fuel that may be made from an alcohol-free-sub-grade fuel. FIGS. 2B and 2C further describe, in an exemplary manner, how model spectral data (e.g., absorbance data) may be used to determine a property value for an alcohol-blended-product fuel which may be made using the method 20. In some embodiments, an alcohol-blended-product fuel may be made by adding a predetermined amount of a solution of an alcohol to an alcohol-free-sub-grade fuel. For example, ethanol may be added as a denatured solution of ethanol which may include about 97% by volume ethanol or some other level of purity. Ethanol may be added in an amount so that the product fuel includes about 10% ethanol by volume. More generally, in some embodiments, other amounts of ethanol may be added to a sub-grade fuel. For example, in some embodiments, an amount of ethanol of up to about 25% by volume may be added to the sub-grade fuel. Other suitable volumes or alcohols may also be added. For example, amounts of alcohol may be added as appropriate to meet industry standards which may change to include increasing or decreasing amounts of one or more alcohols. Methods and teaching described herein, including, for example, those where matrix effects may be modeled and accounted for, may be applied when developing particular protocols for changing amounts of alcohols or other additives as may be useful or required for changing industry standards.

Method 20 may, as shown in a step 22, include collecting absorbance data for an alcohol-free-sub-grade fuel. In a step 24, the collected absorbance data may be combined with other spectral data to construct data representative of an alcohol-blended-product fuel. For example, in some embodiments, the alcohol may be ethanol intended for addition to the sub-grade fuel in an amount suitable to make a 10% alcohol-blended product fuel. The collected absorbance may be combined with spectral data associated with a 10% by volume solution of ethanol. Constructed absorbance data may, for example, be determined at a given wavelength ($\lambda_1$) using either of Equation 1 or Equation 3 which in this exemplary case may be expressed as shown in Equation 4 and Equation 5 with weighting factors established from the predetermined amount of alcohol intended for use in the product fuel:

Abs.(10% Alcohol Product)($\lambda_1$)=0.90 Abs.(sub-grade fuel)($\lambda_1$)+0.10 Abs.(Alcohol)($\lambda_1$)  (Equation 4)

Abs.(10% Alcohol Product)($\lambda_1$)=0.90 Abs.(sub-grade fuel)($\lambda_1$)+0.10 Abs.(Alcohol)($\lambda_1$)+$j(\lambda)$  (Equation 5)

Further by way of example, FIG. 2B shows Spectral Data A which is hypothetical absorbance data for an alcohol-free-sub-grade fuel. FIG. 2B also shows Spectral Data B which is hypothetical absorbance data for an alcohol. To construct spectral data for the exemplary alcohol-blended-product fuel, the magnitude of absorbance in Spectral Data A at a first wavelength ($\lambda_1$) may be scaled based on the weighting coefficient of 0.90 reflecting the predetermined volume fraction of added sub-grade fuel. For example, in some embodiments, the absorbance value at a given wavelength may be multiplied by the weighting coefficient. Spectral Data B may, for example, be downloaded from a memory database and scaled based on a weighting coefficient of 0.10 according to the volume fraction of alcohol to be included in the alcohol-blended-product fuel. For example, the absorbance value at a given wavelength may be multiplied by the weighing coefficient. The scaled absorbance data may then be combined. For example, the scaled absorbance data may be added together to determine a constructed value of absorbance at the wavelength ($\lambda_1$). The aforementioned calculation may be repeated at other wavelengths and used to determine constructed spectral data (e.g., Spectral Data C), which may include a spectrum or one or more parts of a spectrum suitable for use with available calibration data.

In the step 26, calibration data relating to one or more primary or non-spectrographic properties to spectral data may be used to determine one or more property values for an alcohol-blended product fuel. For example, as shown in FIG. 2C, spectral-absorbance data may be constructed and may include data including a desired spectral region which, in this example, may be conveniently expressed as the wavelength range bounded by wavelengths (a) and (b). An integrated value may then be determined from the measured absorbance data using integration boundaries (e.g., the wavelengths (a) and (b)) for the desired spectral region. For example, an integrated value of $X_1$ is shown in the model data of FIG. 2C. The integrated value $X_1$ may be compared to calibration data collected from any number of chemically-similar reference samples. For example, aggregate data may be collected for a number of reference samples each subjected to both primary (non-spectrographic testing) and spectrographic testing. For example, for the reference samples, an integrated value bounded by the aforementioned wavelengths (a) and (b) may be determined and paired to a corresponding property value (such as a RON value). The resulting aggregate data (e.g., relating the RON value to the integrated value) for the reference fuels may be used to generate a correlation line or other correlation model. The integrated value $X_1$ derived from the constructed spectrum may then be compared to the generated correlation line and related to a non-spectrographic property value. For example, in this hypothetical case, a RON value of 91.80 may be determined.

Referring back to FIG. 2A, in the step 28, the method 20 may include determining if the one or more property values are within one or more acceptable specification limits. For example, in some embodiments, to be within acceptable specification limits, a certain property value may be above a minimum property value threshold, below a maximum property value threshold, or between both a minimum property value threshold and a maximum property value threshold. For example, it may be determined that the above RON value is within acceptable limits and the sub-grade fuel may then be transported (step 32) using, for example, a pipeline and directed to a distribution center. Alcohol may then be added to make the product fuel as shown in the step 34. Alternatively, it may be found that one or more determined property values are not within specification limits, and as shown in step 30, appropriate steps may be taken to modify the sub-grade fuel. For example, one or more additional blending or other refining steps may be executed to make a sub-grade fuel suitably configured such that adding alcohol will produce a fuel within specification limits. It should be noted that while alcohol is a fuel component illustrated by example in method 20, the method may be used, for example, with any fuel component that is advantageously added at a certain point downstream of a refinery in a distribution chain, including, for example, after a fuel traverses a pipeline. For example, corrosive materials and/or other additives that may either negatively affect piping material or that present particular problems if leaked to the environment may sometimes be advantageously added downstream of a refinery and pipeline.

As described above, in some embodiments, methods herein may include use of one or more correction factors j ($\lambda$). Generation and use of correction factors j ($\lambda$) is also described herein including in reference to FIGS. 3-6. For example, physically-blended-reference-fuel samples may be collected and compared to constructed spectra. In some embodiments, physically-blended-reference-fuel samples may be collected over time or when validating methods herein, including, for example, when collecting calibration data relating spectral data and non-spectrographic properties. Physically-blended-reference-fuel samples may also be used to create reference spectra used to determine correction factors j ($\lambda$) or j ($\lambda$, c). In some embodiments, physically-blended-reference-fuel samples may be collected in order to model matrix effects between a fuel component and a certain fuel. Matrix effects may be determined for a fuel component and a certain fuel at one or more fuel component amounts or across an amount range. For example, in some embodiments, various physically-blended-reference-fuel samples including ethanol may be collected across an ethanol amount range such as between about 1% by volume to about 25% by volume. Those samples may be made and tested in order to determine matrix effects for ethanol, and to determine whether an ethanol absorbance spectrum may add linearly or non-linearly to a given fuel to which ethanol may be added.

Figure 3:
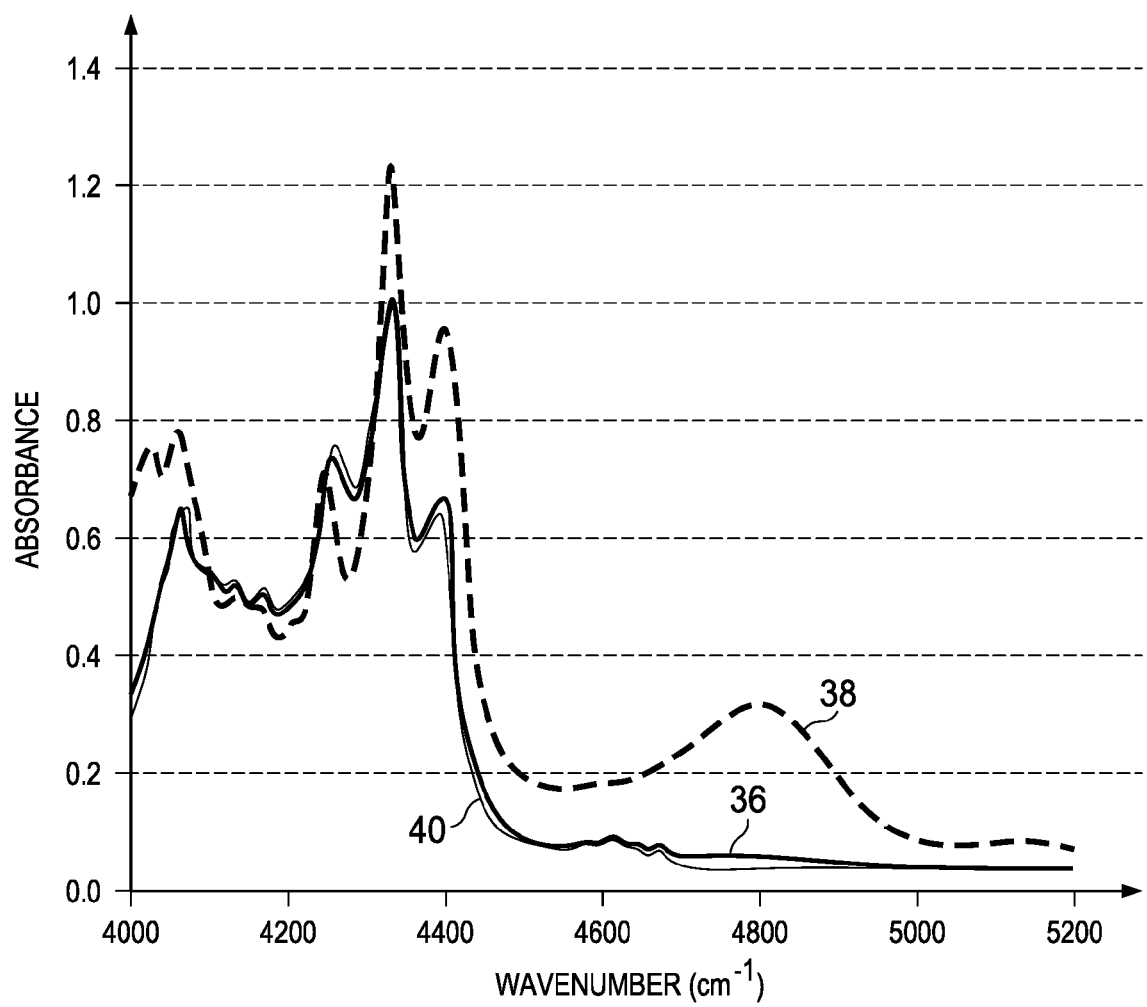
FIG. 3 illustrates various spectra including a spectrum of a physically blended ethanol-product fuel, a spectrum for an ethanol stock solution, and a spectrum of an alcohol-free sub-grade fuel.
Figure 4:
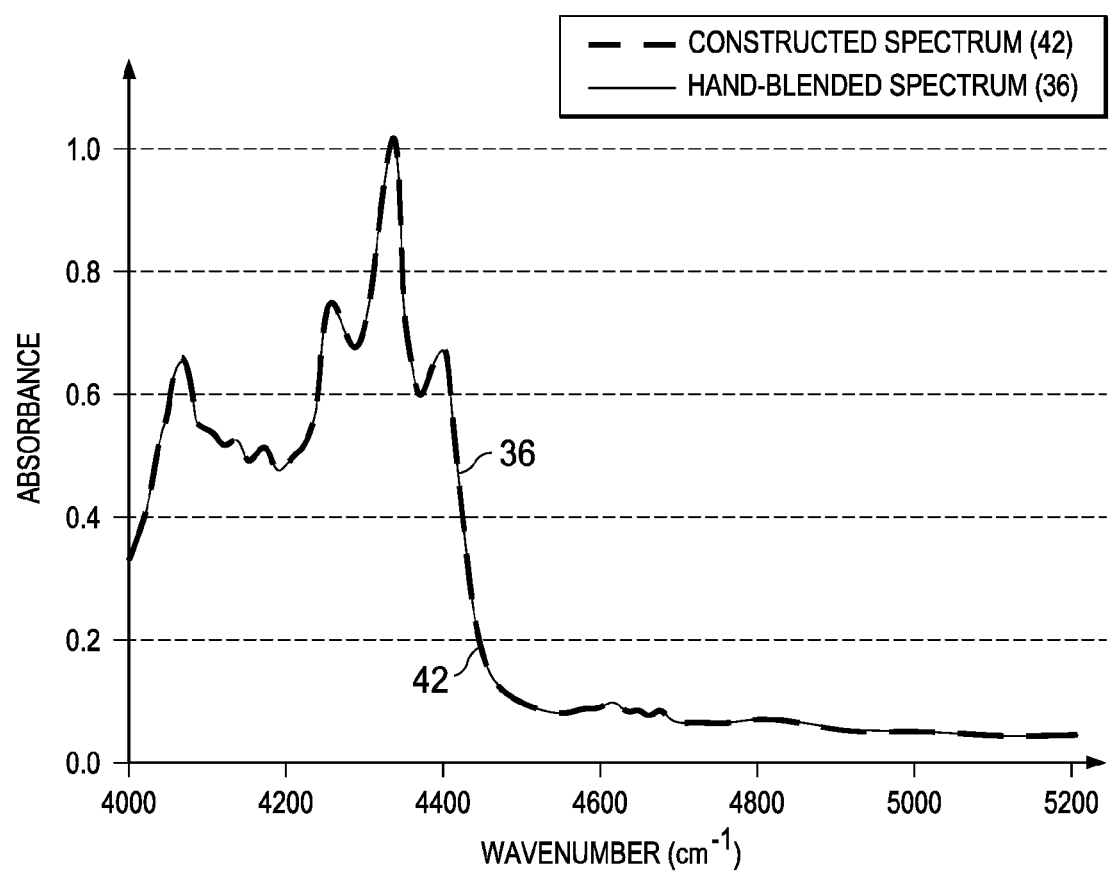
FIG. 4 illustrates constructed spectral data representative of an ethanol-blended-product fuel overlaid with the physically blended ethanol-product fuel spectrum shown in FIG. 3.

FIG. 3 shows spectral absorbance data obtained by measurement of various materials including an ethanol containing physically blended (e.g., by hand) 10% by volume reference fuel sample (spectrum 36), an ethanol stock solution (spectrum 38), and an alcohol-free-sub-grade fuel (spectrum 40). The physically blended 10% by volume reference fuel sample in this example is chemically similar to an alcohol-blended-product fuel made by adding ethanol to the alcohol-free-sub-grade fuel from which spectrum 40 was collected. As shown in FIG. 4, the spectra 38, 40 of FIG. 3 may be used to make a constructed spectrum (spectrum 42). For example, using Equation 1 and applying weighting factors as described in Equation 2, the constructed spectrum 42 may be determined. Particularly, the spectrum 42 was determined by applying weighting factors based on included fractions by volume of an alcohol-free-sub-grade fuel ($x_1=0.90$) and ethanol ($x_2=0.10$). In FIG. 4, the physically blended spectrum 36 is shown together with the constructed spectrum 42.

Figure 5:
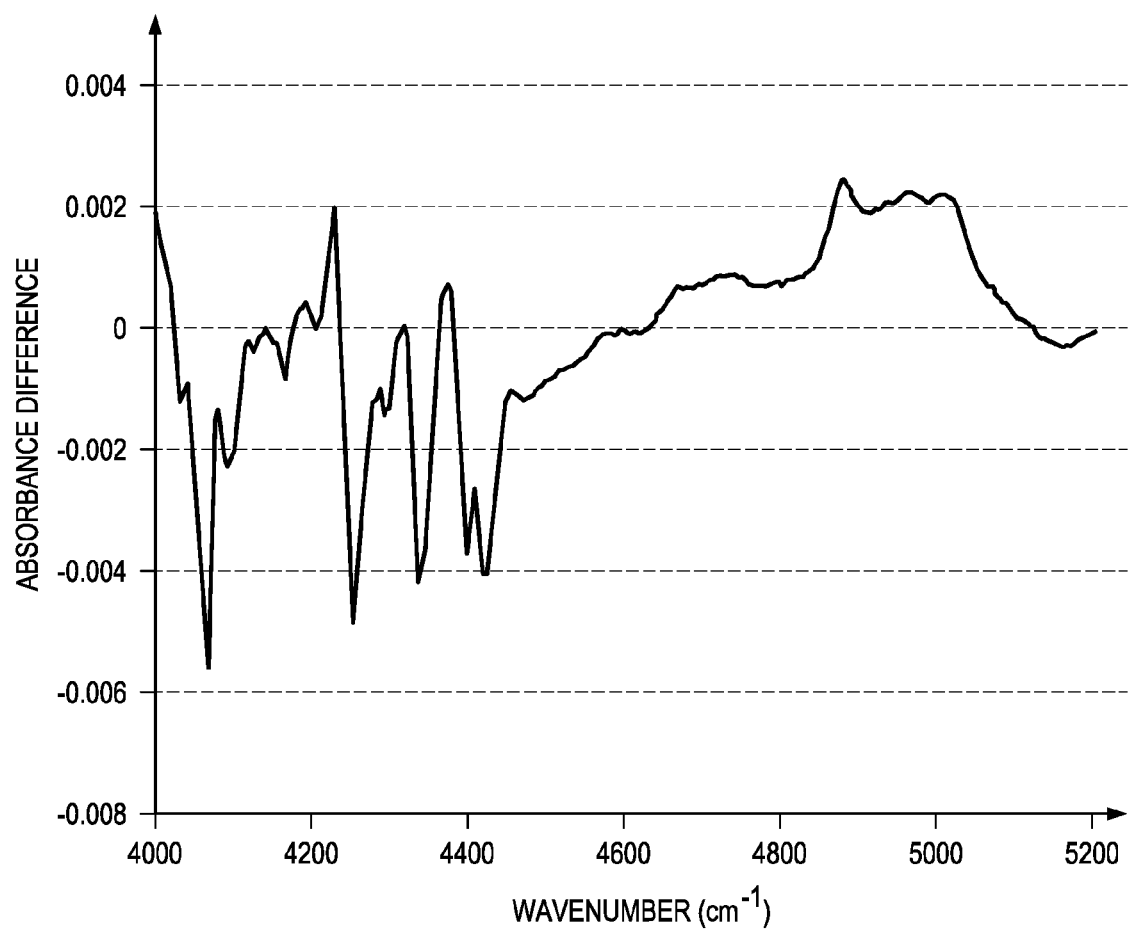
FIG. 5 illustrates a difference spectrum derived from the spectra shown in FIG. 4.

As shown in the FIG. 4, spectrum 36 (e.g., the spectrum derived by testing the physically-blended-ethanol-product fuel sample) and constructed spectrum 42 are similar, and it is difficult, within the scale shown in FIG. 4, to differentiate the two spectra. Small differences between the two spectra 36, 42 are more clearly displayed in FIG. 5 which shows the difference in absorbance over a selected spectral range (conveniently shown in FIG. 5 in units of wavenumbers). Notably, across the selected spectral range, the difference spectrum shown in FIG. 5 is generally less than about 2% of the absorbance shown for the spectrum 36 and significantly lower than 2% in certain spectral regions. Therefore, in this case, matrix effects and non-linearities are small and controlled. Property values may accordingly be determined from a constructed spectrum (e.g., a spectrum constructed based on volume fractions of a first fuel and fuel component additives) with similar reliability as found using other methods based on physical creation of physically-blended-fuel samples which may be a highly precise and accurate methodology. Accordingly, in some embodiments, the difference between a constructed spectrum and a spectrum from a blended product of which it is representative may be ignored. For example, in some embodiments, spectral data constructed in methods herein (e.g., as shown in the steps 14 and 24 of the methods 10 and 20) may be made without consideration of matrix specific nonlinearities and without including a correction factor $j(\lambda)$.

Figure 6:
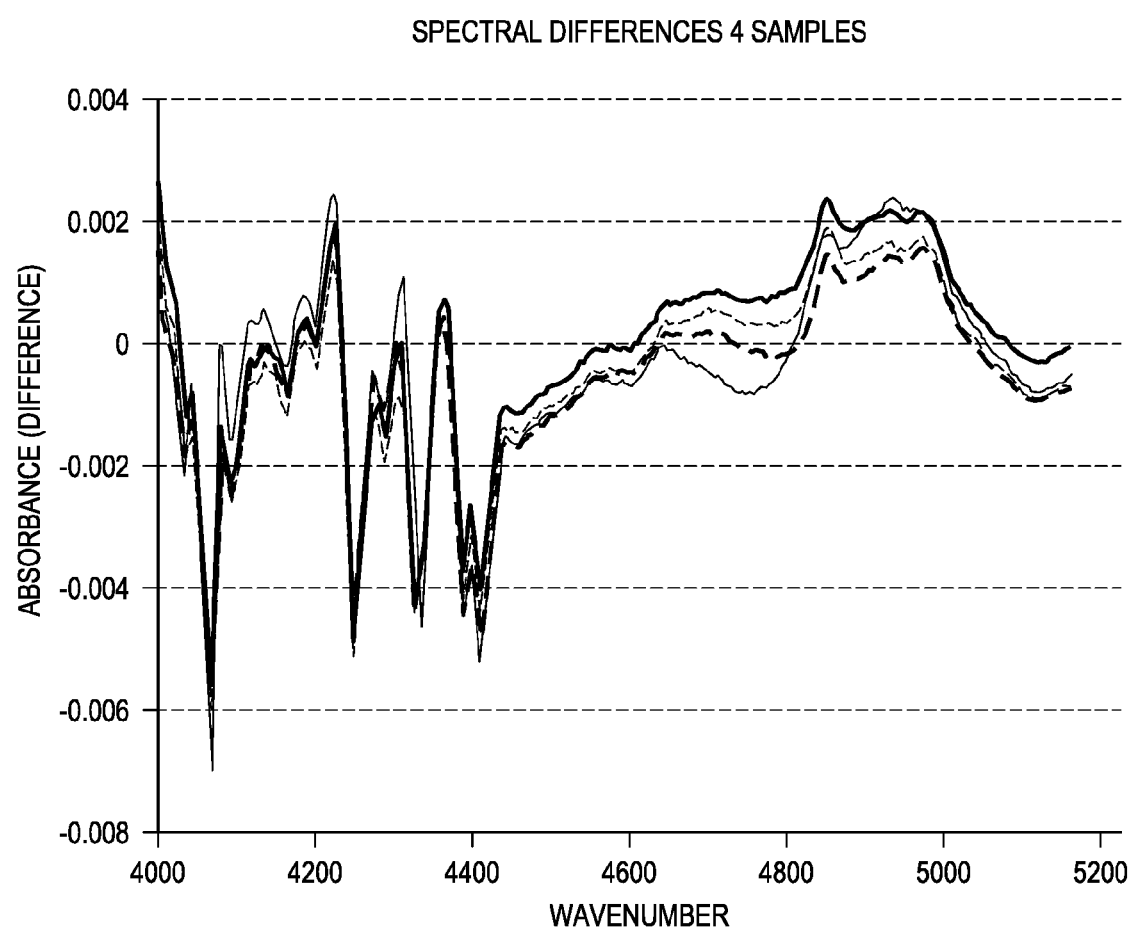
FIG. 6 illustrates a number of difference spectra for multiple product runs.

FIG. 6 indicates results obtained for repeated comparison of multiple physically blended reference-fuel samples including 10% by volume ethanol to a constructed spectrum derived from multiple runs of an alcohol-free-sub-grade fuel. Importantly, the various difference spectra shown in FIG. 6 are similar in shape. The difference between a constructed spectrum and a spectrum collected for a physically-blended-reference-fuel sample may generally be associated with matrix effects between added components and components of the measured fuel (e.g., sub-grade fuel) and associated non-linearities. As evident from the data in FIG. 6, matrix interactions between a sub-grade fuel and added components may be repeatable and thus reliably characterized. Importantly, because such differences may be repeatable, a correction factor $j(\lambda)$, which may be used to account for matrix effects, may be reliably determined from one or more difference spectra. In some embodiments of methods herein, an empirically derived correction factor $j(\lambda)$ may be determined. For example, $j(\lambda)$ may be empirically set to be proportional to the magnitude of a difference spectrum or an average difference spectrum obtained by pooling data from a number of blended reference products and constructed spectra. The magnitude of the correction factor $j(\lambda)$ as a function of wavelength (or other convenient spectral unit) may, for example, be determined based on a difference spectrum, average difference spectrum, or other statistical metric of various difference spectra, and assigned a positive or negative value as appropriate to improve spectral fit between collected spectra and constructed spectra. In some embodiments, a wavelength dependence of a correction factor $j(\lambda)$ may be fit to one or more functions over one or more wavelength intervals. For example, at least over certain portions of data, a difference spectrum may be fit to a polynomial or other function, and $j(\lambda)$ determined accordingly based on a curve fit. Further by way of example, as evident from the data shown in FIG. 6, difference spectra within a band of frequencies between about 4500 $cm^{-1}$ to about 4600 $cm^{-1}$ may be linearly fit.

In some embodiments, a dependence of $j(\lambda)$ may be modeled for different amounts of a fuel component added in different physically-blended-reference-fuel samples. For example, physically-blended-reference-fuel samples with different amounts of an added fuel component may be tested. The dependence of $j(\lambda, c)$ may then be determined by fitting the data to a selected function. For example, values of $j(\lambda)$ for different fuel component amounts may be fit to a linear, polynomial or other convenient function to model the concentration dependence of the various matrix effects that may be present. Therefore, constructed spectra that include a correction for non-linearities may be made for different concentrations of fuel component addition even if empirical data is not available at the particular fuel component concentration intended for addition. For example, for ethanol-blended product fuels of a certain type and/or grade, difference spectra (e.g., as generated from spectra for physically-blended reference-fuel samples and from constructed spectra based on measurement of appropriate sub-grade fuels) may generally be repeatable at a given ethanol concentration. Therefore, matrix effects for ethanol may be well-modeled based on correction factors $j(\lambda, c)$ that extend over a range of added ethanol amounts including near about 10% by volume such as up to about 25% by volume.

In some embodiments, the correction factors $j(\lambda)$ or $j(\lambda, c)$ may be derived from spectra for reference samples for a certain refinery, type of fuel, grade of fuel, or gasoline type. And, generally, by collecting reference fuels of a particular type, chemical similarity to associated fuels may be determined, and correction of matrix effects may be more reliable. In some embodiments, a wavelength-dependent correction factor $j(\lambda)$ may be derived based on data for one or more types of gasoline blends and/or determined for one or more refineries. For example, a type of fuel may be dependent upon the refinery location, gasoline grade (e.g., regular/premium), gasoline type (e.g., RFG (ReFormulated Gasoline), RBOB (Reformulated Blendstock for Oxygenate Blending), Conventional, CARB (California Air Resources Board), CARBOB (California Air Resources Blendstock for Oxygenate Blending)), and season (e.g., winter, summer). For example, a refinery could thus have several separate correction factors $j(\lambda)$ or $j(\lambda, c)$ that would cover all or some of its specific types, grades and seasons of gasoline, and these calibrations may be applied accordingly.

Figure 7:
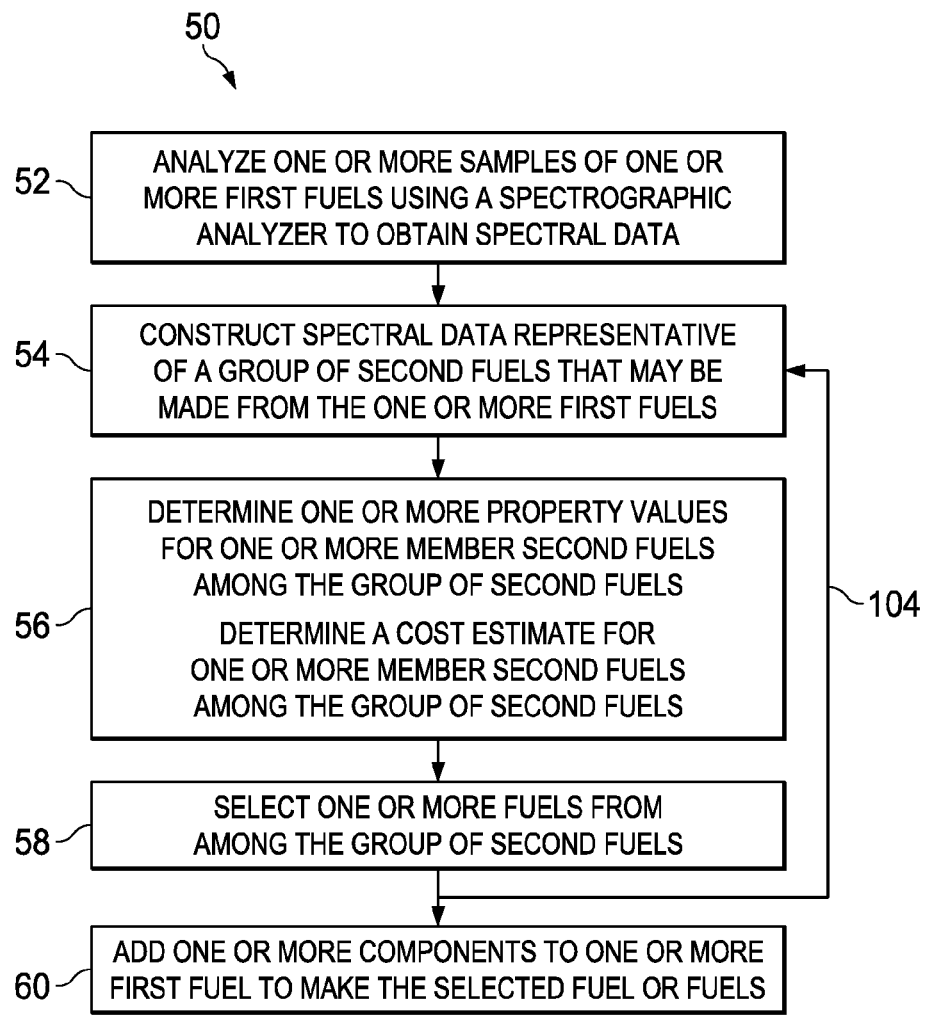
FIG. 7 illustrates embodiments of another method of deriving one or more property values of a fuel.

FIG. 7 illustrates exemplary embodiments of a method 50 for determining property values of a group of second fuels that may be made from one or more first fuels and for selecting a second fuel from among the group of second fuels. The second fuels described in method 50 may be more-processed fuels than first fuels. Accordingly, first fuels, when referenced with respect to second fuels, may also be referred to as less-processed fuels. The second fuels described in method 50 may be made by adding one or more fuel components to one or more first fuels. However, property values for the second fuels may be determined without needing to physically make the second fuel. Accordingly, it should be understood that some second fuels may be referred to herein, but the second fuel or samples of the second fuel may not necessarily be made. For example, using method 50, one may determine that one or more second fuels would have properties that would make it inferior to one or more other second fuels. And, only preferred second fuels or an optimum second fuel may be made.

In a step 52, one or more samples of one or more first fuels may be collected and spectrographically analyzed to provide spectral data. Procedures for spectrographic analysis of a first fuel are also described in greater detail in other methods herein, including, for example, in reference to step 12 of the method 10. In some embodiments, method 50 may be applied using a single first fuel. For example, method 50 may be used to determine an ideal blending protocol for making a second fuel from an available first fuel. However, method 50 may also include embodiments wherein two or more first fuels may be available. For example, some embodiments herein may be useful in determining whether a given first fuel among several different first fuels may be optimally used to make one of several different possible second fuels.

In a step 54, spectral data representative of a group of second fuels may be constructed. Construction of spectral data in step 54 may include obtaining spectral data for one or more fuel components. For example, in some embodiments, to obtain spectral data for one or more fuel components, spectral data may be accessed from a spectral library, spectral data may be obtained by physically testing fuel component samples, or a combination of both procedures may be used. Upon obtaining spectral data for fuel components, spectral data representative of the second fuel may then be constructed in additional parts of step 54. Construction of spectral data representative of a second fuel is also described in greater detail in other methods herein, including, for example, in reference to step 14 of the method 10.

In some embodiments, particular advantages of method 50 may be found wherein property values are determined for more than one second fuel. For example, some members of a group of second fuels may include a common fuel component. However, it may be useful to vary the amount of that fuel component over a certain range. In some embodiments, spectral data may be constructed (step 54) for a group of second fuels by varying weighting factors (such as described in Equation 2) over a test range. For example, a weighting factor $x_i$ may be varied over a range of +/−0.5%, +/−1%, +/−2%, +/−5% or varied over another range from a base $x_i$ value. In some embodiments, it may be feasible to create spectral data indicative of varying amounts of a component, wherein component amounts are varied in a substantially continuous manner over some range. For example, in some embodiments, spectral data may be constructed for second fuels that include varying amounts of ethanol (e.g., ethanol may be varied in intervals of 0.1% or at some other desired resolution) over a range of between about 8% to about 12%. In some embodiments, in addition to weighting factors, concentration dependent correction factors $j$ ($\lambda$, c) may also be adjusted to create constructed spectral data representative of a group of second fuels.

In some embodiments, spectral data may be constructed (step 54) to be representative of a group of second fuels wherein member fuels of the group may include different identities and/or amounts of one or more added fuel components. For example, in order to change one or more fuel properties, as may be part of one or more blending operations executed at a certain stage of refinery production, different additives or groups of additives may alternatively be added to a first fuel. However, it may sometimes be the case that use of one additive or group of additives as opposed to use of another additive or group of additives may yield a better result. For example, if one were to make samples of fuels based on alternative addition scenarios, one may realize when using one group of additives to adjust one or more fuel properties that other properties are less affected or affected in a more desired way than when using another group. Some embodiments of method 50 are ideally suited to determine ideal groups of one or more additives that may be added at a stage of refinery production. For example, in some embodiments, spectral data may be constructed (step 54) that may be indicative of two or more subgroups of fuels included among an overall group of second fuels. That spectral data may be designed to test whether a certain additive or combination of additives (as may be associated with one subgroup of fuels) may be better suited to adjust one or more properties or better suited for use at a certain stage of fuel production than another additive or combination of additives (as may be associated with another subgroup of fuels).

In some embodiments, among a group of second fuels for which spectral data is constructed in step 54, the identity and/or amounts of some fuel components may be fixed and other identities and/or amounts may be varied. For example, in some embodiments, method 50 may be used to select and/or make a certain alcohol-blended-product fuel from among a group of alcohol-blended-product fuels. In creation or modeling of various alcohol-blended-product fuels, an alcohol, such as ethanol, may be added at a fixed amount to a sub-grade fuel at a downstream location from a refinery. Accordingly, in a group of second fuels for which spectral data is constructed in step 54, ethanol may be set at that fixed amount or fixed at that amount in one or more end stages in one or more blending scenarios. Amounts or identities of other fuel components may be varied among second fuels in the group. Some of those embodiments may be particularly valuable where property values are modeled through multiple blending operations. For example, where multiple blending operations are modeled, problems that may physically manifest following end-component addition may be understood and corrected early in the blending process.

In a step 56, calibration data relating primary or non-spectrographic properties to spectral data may be accessed, and property values for one or more member second fuels among the group of second fuels for which spectral data was constructed may be determined. In some embodiments, those property values may be determined without needing to physically mix test samples of some or all of the second fuels. Operations executed to determine property values for second fuels are described in greater detail in other methods herein, including, for example, in reference to step 16 of the method 10.

In some embodiments, in the step 56, a cost associated with making one or more member fuels among the group of second fuels may also be determined. For example, in some embodiments, the material cost of fuel components and/or first fuels may be added together in appropriate amounts for one or more member second fuels among the group of second fuels. Other more complicated models may also be used including, for example, models that may consider labor costs, costs in maintaining the supply of components, and other associated costs.

Figure 8:
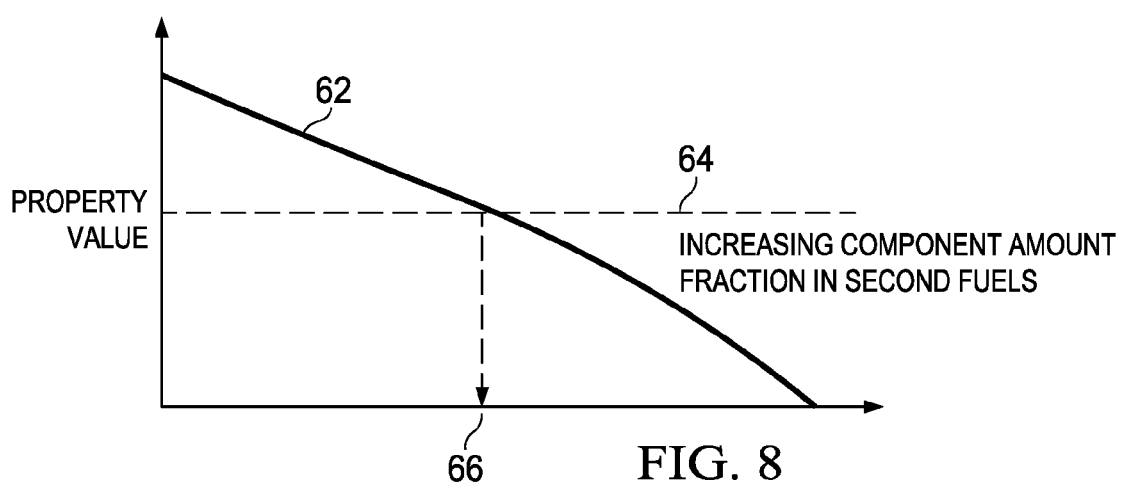
FIG. 8 illustrates how a model property value may be dependent on increasing component amount fractions as may be determined in some embodiments of methods illustrated in FIG. 7.

In a step 58, a fuel (including, in some embodiments, more than one fuel) may be selected from among a group of second fuels (e.g., second fuels for which spectra were constructed and property values determined). To select a fuel in step 58, any of various suitable criteria may be used including, for example, matching of one or more property values of a selected fuel with one or more desired property values. For example, to determine a property value dependence on amount fraction, weighting factors $x_i$ for a certain component may be varied over a certain range. FIG. 8 shows a dependence of a property value versus amount fractions of a component included in different second fuels. Particularly, model curve 62 shows a hypothetical dependence of a single property value against amount fraction of a component in second fuels. In FIG. 8, a desired or target value 64 of the example property is shown as a dashed line. To create a fuel that meets the property value 64, a component may be added (as shown in step 60) at a desired amount fraction 66. A property value of a fuel property may also change based on more than one added fuel component. Accordingly, the dependence of a property value versus different amount fractions for the more than one fuel component may also be determined. More generally, in the step 58, a second fuel may be selected based on attributes of the fuel or characteristics of making the fuel including, for example, cost of making the fuel, optimum process latitude with respect to one or more fuel property values, minimized property value shifts, minimized risk of corrective blending operations, other attributes and combinations thereof.

As shown in step 60 (FIG. 7), in some embodiments, once one or more second fuels are selected from a group of second fuels in the step 58, the one or more second fuels may be made. Thus, it should be understood that the method 50 may be used to select and make one or more fuels. However, method 50 may also be a method of modeling the properties of one or more fuels.

In some embodiments, property values may be determined for one or more fuels that may be made in additional blending steps. For example, as shown by arrow 104, constructed spectral data representative of other fuels that may be made from the one or more selected fuels (e.g., by adding still further fuel components) may be created. In those embodiments, the spectral data for the selected fuel (which was previously calculated in step 54 and is thus available for later calculations) may be combined with spectral data for one or more of the still further fuel components. Thus, in some embodiments, method 50 may operate in an iterative manner modeling property values for a series of blending operations.

Figure 9:
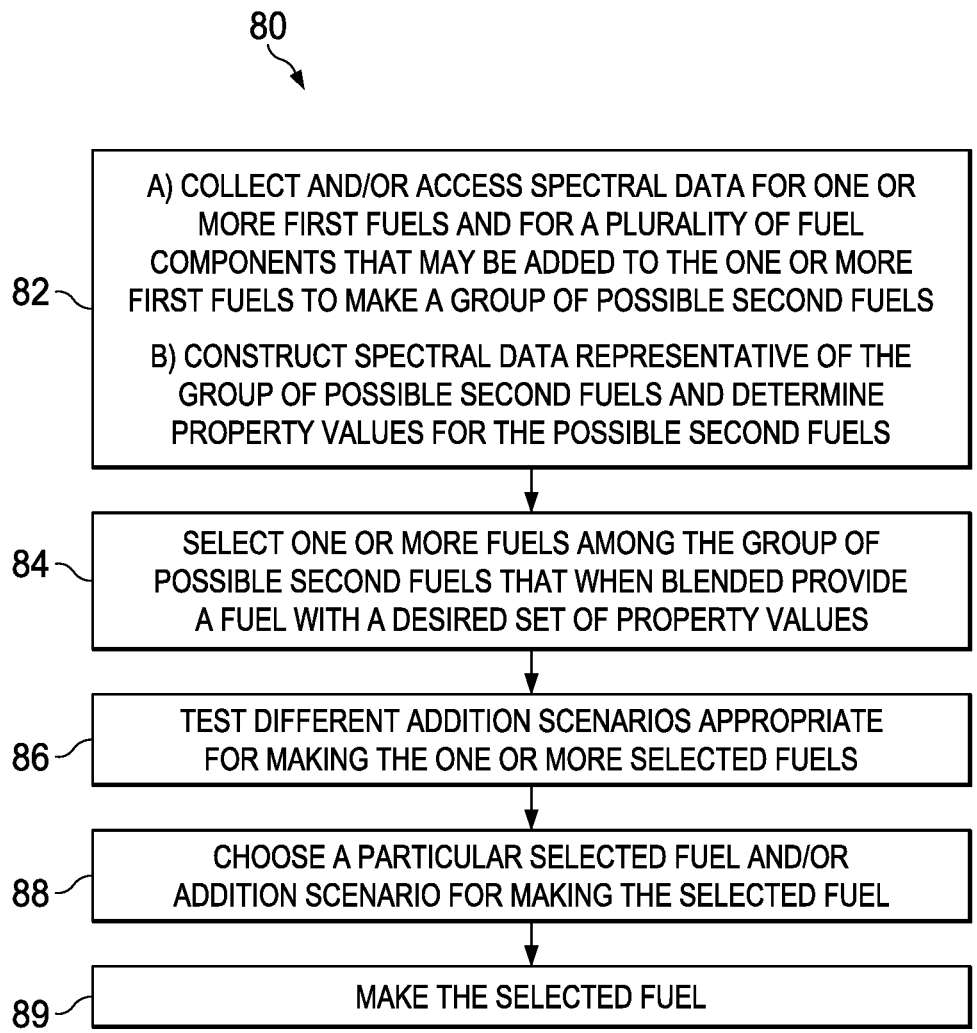
FIG. 9 illustrates embodiments of a method for selecting and making a fuel.
Figure 10:
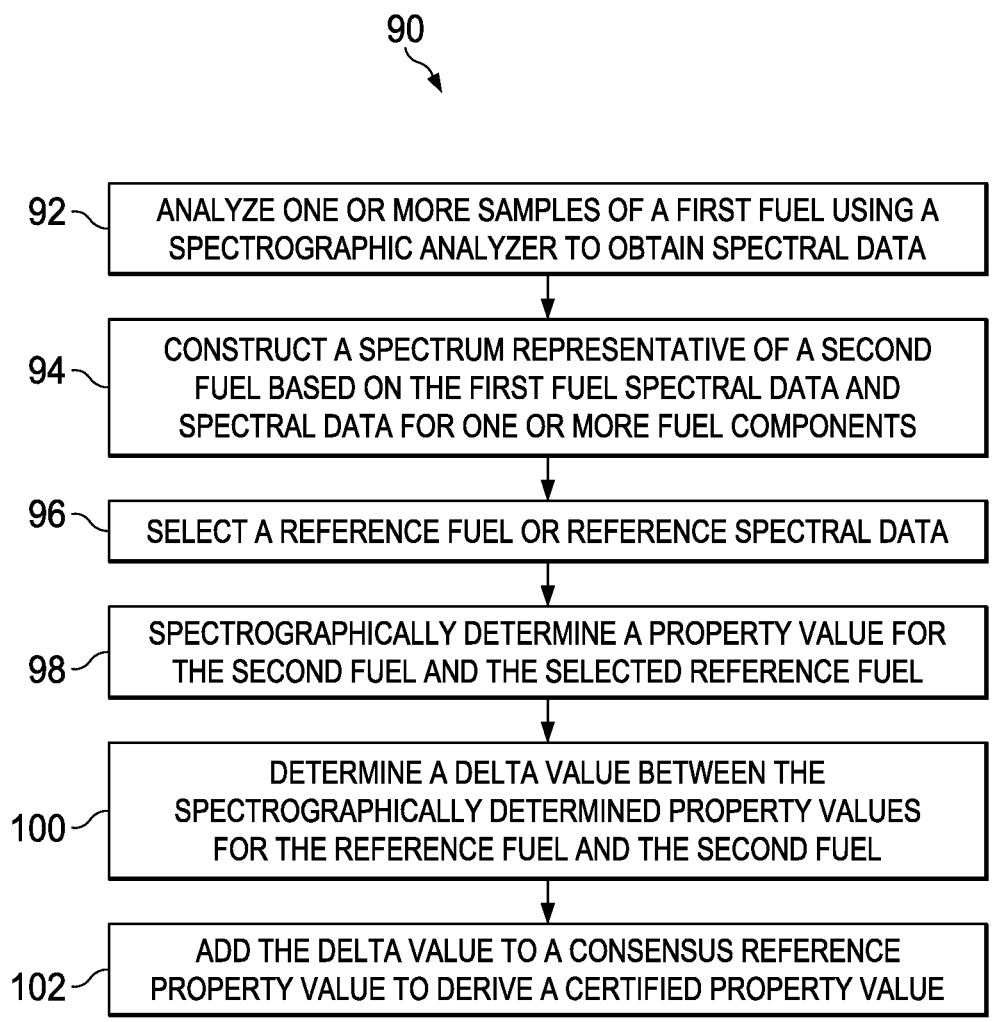
FIG. 10 illustrates embodiments of a method of deriving one or more property values of a fuel using a direct-match spectrographic technique.

FIG. 9 illustrates exemplary embodiments of another method 80 for modeling blending operations in refinery processing. In a step 82, one or more samples of one or more first fuels may be collected and spectrographically analyzed to provide spectral data. Alternatively, in some embodiments, spectral data for one or more first fuels may be accessed and downloaded for modeling from a database. Further in step 82, spectral data for fuel components may be accessed from a spectral library and/or spectral data may be obtained by physically testing samples of fuel components. In some embodiments, using the collected and/or accessed spectral data, representative spectral data for a group of possible second fuels that may be made using various amounts and/or identities of the fuel components may be constructed. Operations that may be executed as part of step 82 are further described in greater detail in other methods described herein, including, for example, in reference to steps 12-16 of the method 10.

In some embodiments, the group of possible second fuels considered in step 82 may be more processed fuels than first fuels. In some embodiments, the group of possible second fuels considered in step 82 may be fuels that typically would be made from first fuels therein in several blending steps. For example, in some embodiments, method 80 may be used to model addition scenarios useful to modify multiple property values using a multitude of different fuel components including those that may be added in one or more steps.

In a step 84, one or more fuels among the possible second fuels may be selected. For example, a selected second fuel may have a desired set of property values that is deemed useful in a product fuel or other fuel.

In a step 86, different addition scenarios may be tested for making the one or more selected fuels. For example, a computer program may be set up to run different simulations including various addition strategies. In the various addition scenarios, property values may be determined for one or more intermediate-blended fuels.

In a step 88, a particular selected fuel and/or addition scenario may be chosen. For example, in some embodiments, property values may be tracked for various intermediate-blended fuels that may be made in a given addition scenario. And, for example, an addition scenario may be chosen wherein property value shifts during a blending sequence are controlled. In some embodiments, a decision to choose one addition scenario over another may not only be based on overall control of property value shifts. Rather, a relative cost of counteracting unexpected property shifts may be included in choosing one or more addition scenarios. For example, based on material cost, blending run times, or other criteria it may be known that the cost of correcting certain property value shifts is higher or more difficult than that of correcting other property values. Accordingly, one addition scenario may be more desired than another addition scenario because the desired addition scenario controls property value shifts more closely in blending operations that are more costly to execute or that adjust properties that are more difficult to correct.

In a step 89, a selected second fuel may be made. As described above, not only may a second fuel be selected and made based on properties of the fuel, but also addition scenarios may be modeled. Moreover, that modeling may be done at a high level of rigor and detail. For example, one may, at a desired level of resolution, determine property values and shifts for any number of intermediate-blended fuels. In some embodiments, it may be deemed that physical samples should be collected for one or more intermediate-blended fuels or that addition in one or more steps should be made slowly so that samples may be taken therefrom and tested.

In some embodiments, methods herein may be integrated together with direct-match spectrographic methods. For example, as described in the references incorporated herein, spectrographic analyzers having location- and matrix-specific calibrations may be used by refineries to determine product properties. Because such calibrations may be location- and matrix-specific, methods using spectrographic analyzers may not comply with the requirements of existing industry standard methods of certifying a fuel product as having specific properties. Regulatory agencies may thus refuse to accept test results based on spectrographic analysis as valid for product certification. In addition, location- and matrix-specific calibrations may make it difficult to compare data between different instruments, sampling or processing techniques, and laboratories, which may, for example, be physically located at the same location or at different locations. Direct-match spectrographic methods may be used to address the aforementioned problems and concerns.

Direct-match spectrographic methods may, in some embodiments, incorporate the use of global-calibration data. For example, one way to resolve location- and matrix-specific biases may be to generate global calibration values. A global calibration may be based on spectral and analytical data from a variety of location- and matrix-specific calibrations. "Global" may refer to worldwide refinery product, or as much refinery product as may be available from participating refineries. In some embodiments, global calibration data may include data from a data set of participating users, and may include for example, data produced from a range of blend components, fuel properties, or a combination of both. In some embodiments, the global calibration values may be based on location- and matrix-specific data for a particular product fuel, such as gasoline, produced by a variety of refineries, or may be based on a variety of products from one or more refineries. Global calibration data for gasoline may, for example, include data from a variety of locations and from a variety of product matrices. A group of refineries may aggregate their location- and matrix-specific calibrations and use a statistical tool to develop global calibration values. For example, a multivariate regression analysis, such as that described in ASTM E1655, may be used to develop global calibration values for various properties. Global calibration data may further be included in a globally-calibrated spectrometer.

In some embodiments herein, global calibration data may be included in methods used to determine property values of one fuel based on spectral data collected from another fuel. For example, as described herein, global-calibration data may be substituted for other calibration data and used to determine property values for any of the various fuels described herein including sub-grade fuels, intermediate fuels, product fuels, and other fuels. For example, in some embodiments, an alcohol-free-sub-grade fuel may be made at a refinery, and properties of an alcohol-blended-product fuel (which may be made by addition of alcohol downstream of the refinery), may be determined using methods that may incorporate global calibration data.

In some embodiments herein of methods that include use of global calibration data for determining property values, a reference product may be tested together with construction of spectral data representative of a fuel for which property value information is desired. For example, a reference product that is chemically similar to the fuel for which property value information is desired may be spectrographically tested.

In some embodiments, a reference fuel may have a composition including matrix components that is related to the refinery from which it is collected. The reference fuel may then undergo primary testing using a non-spectrographic instrument or analyzer to determine the reference fuel's property values. Reference values may also be determined in other ways. For example, a refinery may choose among various levels of rigor in primary testing to determine reference values: e.g., laboratory reference values, consensus reference values and semi-consensus reference values may be used in some embodiments herein. Those values and methods incorporating those values are described in greater detail in U.S. Pat. Nos. 8,481,942 and 8,735,820, commonly owned by Applicant and incorporated herein.

Continuing with the representative example where property values for an alcohol-blended-product fuel may be determined, a sub-grade fuel may be tested to collect spectral data. The spectral data may be conditioned using a process of spectral construction so that it is representative of an alcohol-blended-product fuel. To qualify the alcohol-blended-product fuel, a test sample of the sub-grade fuel may be spectrographically tested along with a reference sample deemed chemically similar to the alcohol-blended-product fuel.

For example, for batch analysis, the method may comprise (1) obtaining a sample of reference fuel (or prototype fuel as described in the incorporated references) of the same type, grade and season as the sub-grade fuel to be tested; (2) chilling both the reference fuel and the sub-grade fuel in the same manner and for the same length of time; (3) determining the reference fuel properties using the globally-calibrated spectrometer; (4) spectrographically testing the sub-grade fuel, constructing spectral data, and determining properties of the alcohol-blended-product fuel that may be made from the sub-grade fuel using the globally-calibrated spectrometer; and (5) calculating a delta value between the alcohol-blended-product fuel and the reference fuel for each property:

$$\Delta_i = TI_i - RI_i \quad \text{(Equation 6)}$$

Where:
$\Delta_i$=difference between the spectrographically-determined property values of the alcohol-blended-product fuel and the reference fuel $TI_i$=spectrographically-determined property value of the alcohol-blended-product fuel based on testing of a sub-grade fuel and spectral construction (text index)

$RI_i$=spectrographically-determined property value of the reference fuel (reference index)

i=a property, such as MON or RON

The method may further comprise calculating the derived property of the alcohol-blended-product fuel ($T_i$):

$$T_i = \Delta_i + R_i \quad \text{(Equation 7)}$$

Where:
$T_i$=derived property value of the alcohol-blended-product fuel for certification $R_i$=property value of the reference fuel determined by primary testing (e.g., consensus value, laboratory reference value, or semi-consensus value)

FIG. 9 illustrates an exemplary embodiment of a method for direct match comparison of a fuel against a chemically-similar reference fuel including spectral construction. In a step 92, one or more samples of a first fuel may be collected and spectrographically analyzed to provide spectral data. For example, in some embodiments, the first fuel may be selected from a group of fuels including an intermediate fuel, blendstock fuel, sub-grade fuel, or alcohol-free-sub-grade fuel.

In a step 94, spectral data may be constructed that is representative of a second fuel. For example, the second fuel may be a fuel that may be made from the first fuel using some amount of one or more fuel components. In other embodiments, various spectra indicative of a plurality of second fuels, including various identities and/or amounts of one or more fuel components, may be constructed. Constructed spectrum may, for example, be based on any of Equations 1-3, as described herein.

In a step 96, a reference fuel or reference spectral data may be selected. For example, the reference fuel may be selected because it is deemed chemically similar to the second fuel. In some embodiments, a reference fuel may be deemed chemically similar to a second fuel because the fuels share one or more common characteristics selected from the group of characteristics including refinery location of origin, gasoline grade (e.g., regular/premium), gasoline type (e.g., RFG (ReFormulated Gasoline), RBOB (Reformulated Blendstock for Oxygenate Blending), Conventional, CARB (California Air Resources Board), CARBOB (California Air Resources Blendstock for Oxygenate Blending)), and seasonal variation (e.g., winter, summer). For example, in some embodiments, a reference fuel may be deemed similar to a second fuel because the fuels may originate from the same refinery and further are fuels of the same grade, type, or seasonal variation.

In some embodiments, a reference fuel may be deemed chemically similar to a second fuel based on chemical analysis. Or, chemical analysis may corroborate that two fuels that share one or more common characteristics as described above are chemically similar. For example, chemical analysis may include characterization of the reference and second fuel using a spectrographic analyzer or with some other analytical instrument capable of quantitative chemical analysis. Chemically similar products may, for example, have a similar distribution of hydrocarbons such as octane, iso-octane, heptanes, other straight or branched chain hydrocarbons, or combinations thereof.

In some embodiments, spectral data may be used to verify or support a belief that a second fuel is similar to a reference fuel. For example, constructed spectral data may be used to select a particular reference sample from among a group of possible reference samples. For example, a database library may be created that includes one or more spectra for each of a group of reference products. The reference product or products for which spectra are included in a library may comprise all available reference products for which spectral data are available or a group of products that are related because they share a certain characteristic, e.g., production origin at a certain refinery, seasonal grade or type. To select a certain reference product, one or more constructed spectra may be made, and an operator may execute a search of the database to find a particular reference spectrum that most closely resembles the constructed spectrum.

In a step 98, a refinery's laboratory may run a spectrographic test of the reference fuel using a globally-calibrated spectrometer. For example, as shown in Table 2 (which shows hypothetical data), the RON for the reference fuel may be determined to be spectroscopically 92.10. In some embodiments, spectrographic property values may be linked in a database to selected spectral data. As further shown in the step 98, a spectrographically determined property value may be determined for the second fuel. To determine a spectrographic property value for the second fuel, the constructed spectrum (determined in step 94) may be compared to global-calibration data and a property value for the second fuel determined. For example, the RON for the second fuel may be determined to be 92.00. In step 100, the differences, or deltas, between the spectrographically-determined values for the second fuel and reference fuel values may be calculated as in Table 1.

TABLE 1

| TEST | Second Fuel Spectroscopic Determination | Reference Fuel Spectroscopic Determination | Delta | Reference Fuel Consensus Value | Test Result |
|---|---|---|---|---|---|
| RON | 92.00 | 92.10 | −0.10 | 92.21 | 92.11 |
| MON | 82.30 | 81.15 | 1.15 | 82.35 | 83.50 |

Consensus values of the reference fuel may be known because the consensus values may have been previously measured such as in a manner as described herein and as described in the references incorporated herein. As also described in the incorporated references, laboratory reference or semi-consensus values may be used, as well. For example, a consensus value for RON of the reference fuel may be 92.21. In step 102, the RON and MON value deltas may be added to the reference consensus RON and MON values, respectively, to derive the RON and MON values of the test fuel suitable for certification.

Additional information related to the methods and apparatus described herein may be understood in connection with the example provided below.

EXAMPLES

Figure 11:
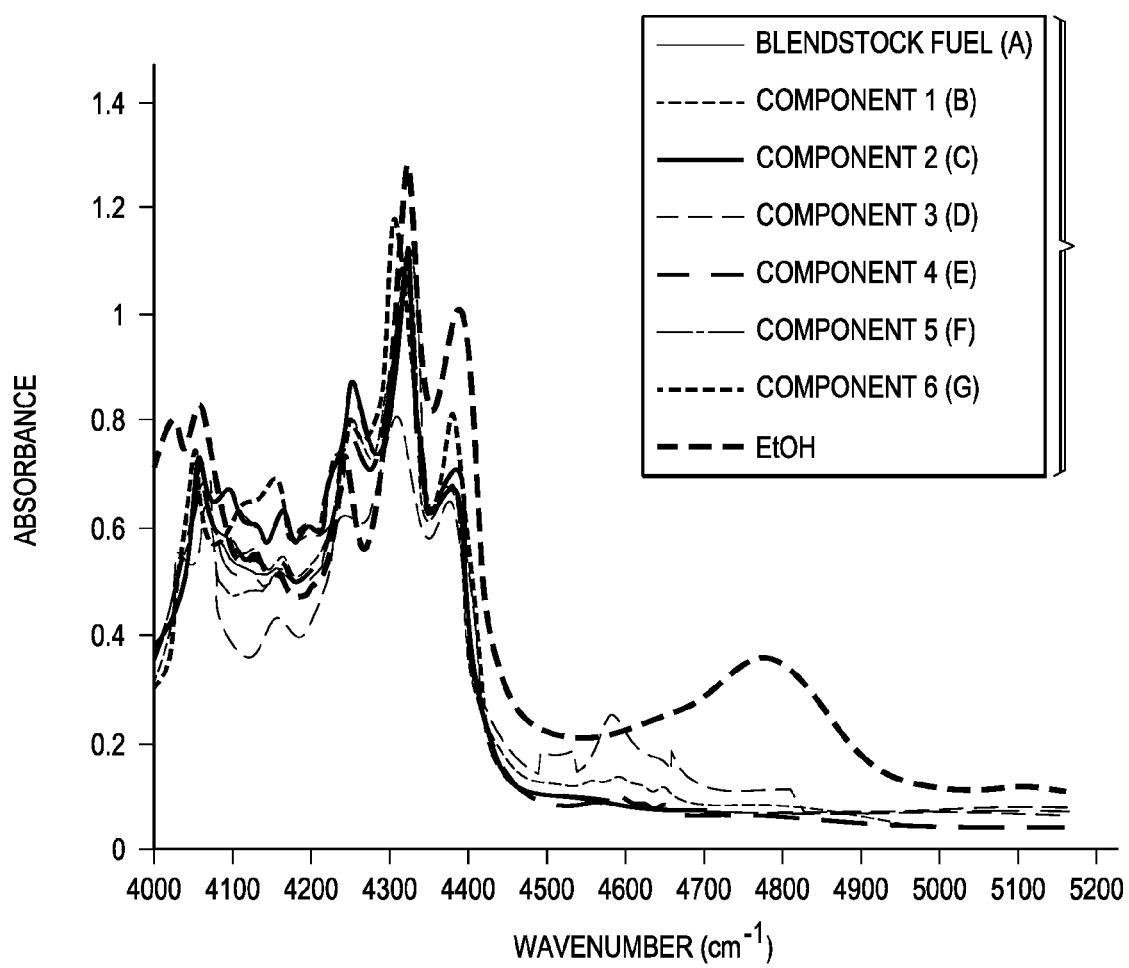
FIG. 11 illustrates various components that may be added to a blendstock fuel to make a product fuel.

A blendstock fuel was made and spectral data collected for the blendstock fuel. Spectral data for the blendstock fuel (A) is shown in FIG. 11 together with spectral data for a number of different components that may be blended with the blendstock fuel. Particularly, FIG. 11 shows a series of 6 different fuel components (B-G) that are mixtures derived from intermediate processing of crude oil. In addition, FIG. 11 shows spectral data for ethanol (EtOH), an additive which may be later added as denatured ethanol of 97% purity by volume. The various components (B-G) may be blended together in any number of steps. In any number of those steps, including intermediate steps before all components (B-G and EtOH) have been added, a spectrum may be constructed. And, using suitable calibration data, property values may then be determined.

Figure 12:
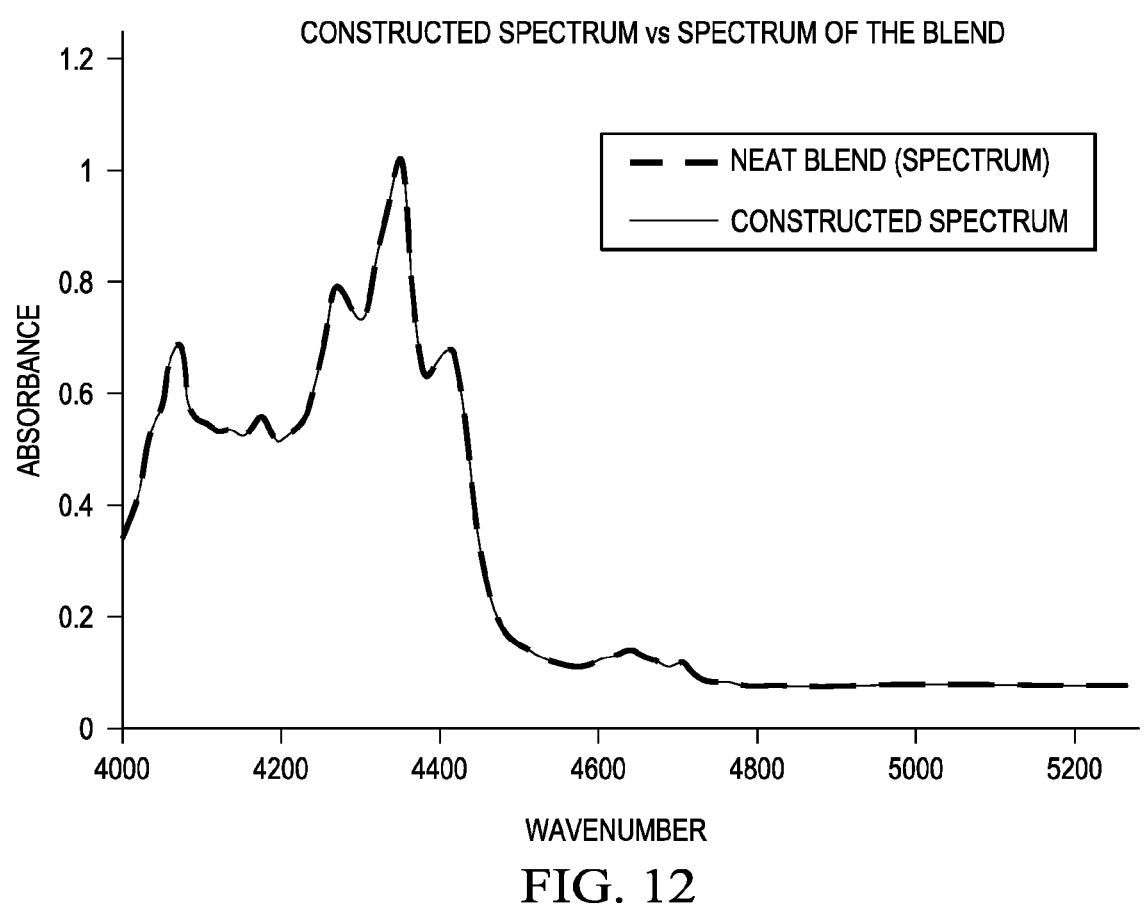
FIG. 12 illustrates constructed spectral data representative of a fuel made by blending the various components and blendstock fuel shown in FIG. 11 overlaid with another spectrum collected from physically mixed fuel components.

For example, in FIG. 12 a constructed spectrum is shown representative of a sample made by blending all of the aforementioned components (B-G) and ethanol with the blendstock fuel. In addition, a neat blend was physically made by addition of the blendstock and aforementioned fuel components and ethanol. In FIG. 12, a spectrum collected by direct measurement of a sample of the neat blend is shown together with the constructed spectrum. The two spectra are very similar and within the scale shown therein it is difficult to see differences between the two spectra. Small differences between the two spectra are more clearly displayed in FIG. 13, which shows a difference spectrum calculated from the data shown in FIG. 12.

Figure 13:
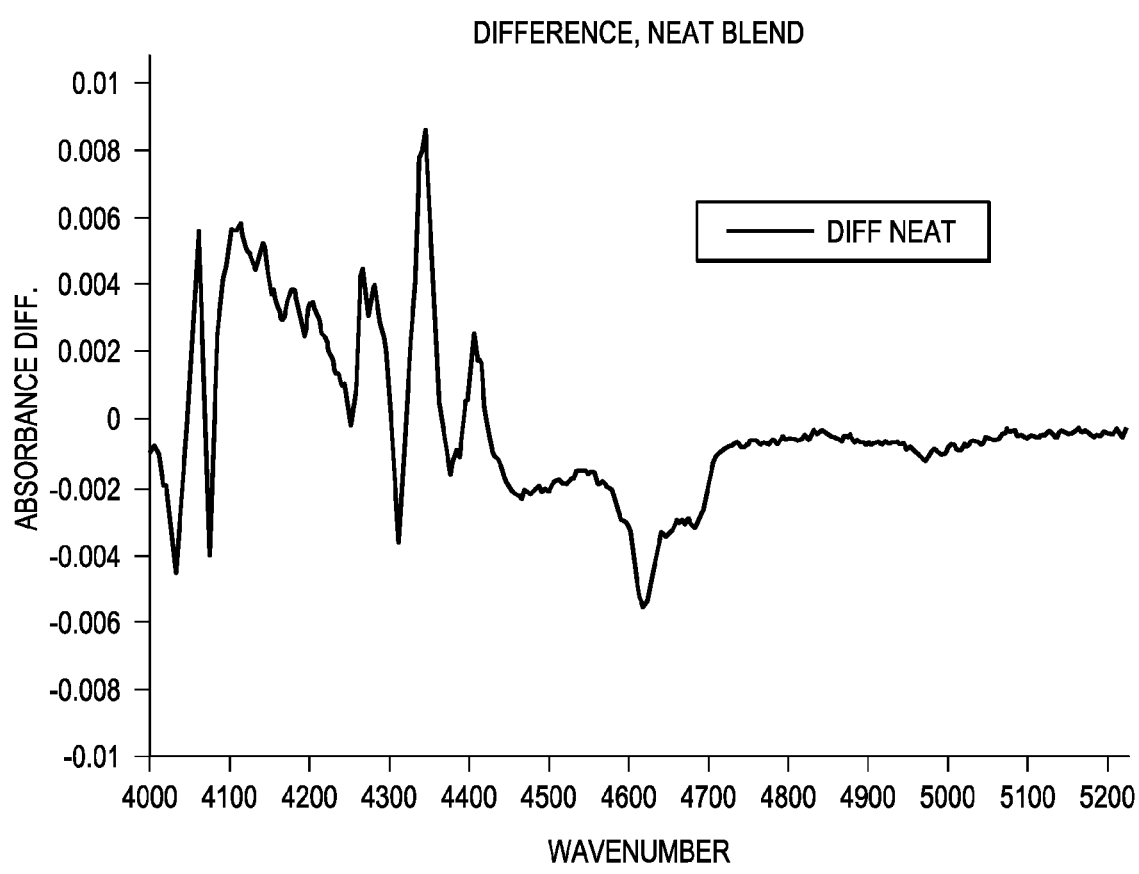
FIG. 13 illustrates a difference spectrum between the two spectra shown in FIG. 12.

Notably, across the spectral range shown in FIG. 13, the difference spectrum is only a small fraction of the absorbance measured for the neat blend. Therefore, matrix effects and associated non-linearities are small and controlled. Property values may accordingly be determined from either of the constructed spectrum or physically blended neat blend. Accordingly, methods based on a constructed spectrum may be used to derive property values without associated sample preparation demanded by methods that physically test an actual hand blend. In addition, property values for intermediate-blended fuels may be determined and various combinations of component addition modeled. For example, property values for intermediate fuels where only some of the above fuel components are added may be tested. Accordingly, property values may be modeled throughout the addition of various fuel components.

Although the present application and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. For example, aspects of different embodiments may be incorporated into other embodiments. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

I claim:

1. A method of qualifying a fuel, the method comprising:
    obtaining spectral data for a first fuel;
    combining the spectral data for said first fuel with spectral data for one or more fuel components to construct spectral data representative of a group of second fuels, said construction comprising weighting the spectral data for said first fuel and the spectral data for said one or more fuel components according to amounts of said first fuel and amounts of said one or more fuel components as suitable for making different members among said group of second fuels;
    determining one or more property values for member second fuels among said group of second fuels by comparing said constructed spectral data to calibration data; and
    qualifying one or more member second fuels from among said group of second fuels based on said one or more property values.

2. The method of claim 1 wherein said group of second fuels includes second fuels that include a varying amount of an adjustable fuel component over a test range.

3. The method of claim 2 wherein said adjustable fuel component is ethanol; and
    wherein said test range includes a range from about 1% to about 25% by volume.

4. The method of claim 3 wherein said adjustable fuel component is varied in a substantially continuous manner over said test range.

5. The method of claim 1 further comprising estimating a cost for making different members among said group of second fuels.

6. A method of preparing a product fuel, the method comprising:
    receiving a subgrade fuel for which first spectral data has been obtained;
    adding a fuel component to the subgrade fuel to make a product fuel qualified according to the method of claim 1.

7. A method of determining a property value of a property for a fuel, the method comprising:
    obtaining spectral data for a first fuel;
    combining the spectral data for said first fuel with spectral data for one or more fuel components to derive constructed spectral data representative of a second fuel, said construction comprising weighting the spectral data for said first fuel and the spectral data for said one or more fuel components suitable for making said second fuel; and
    determining a property value of a property for said second fuel by comparing said constructed spectral data to calibration data in order to determine a property value of a property for said second fuel.

8. The method of claim 7 further comprising adjusting said constructed spectral data based on a wavelength-dependent correction factor.

9. The method of claim 8 wherein said correction factor is empirically derived from one or more difference spectra.

10. The method of claim 8 wherein said correction factor is modeled for different amounts of one or more of said one or more fuel components.

11. The method of claim 7 wherein said spectral data for said one or more fuel components is accessed from a spectral library.

12. The method of claim 7 wherein said spectral data for at least one of said one or more fuel components is derived by spectrographically testing one or more samples of said at least one of said one or more fuel components.

13. The method of claim 7 wherein said first fuel is a sub-grade fuel and said second fuel is an alcohol-blended product fuel.

14. The method of claim 13 wherein said alcohol-blended product fuel includes ethanol in an amount of between about 1% by volume and about 20% by volume.

15. The method of claim 7 wherein said first fuel is a blendstock fuel and said second fuel is either a sub-grade fuel or an ethanol-blended-product fuel.

16. The method of claim 15 wherein said first fuel is a sub-grade fuel configured for transport from a refinery and further configured such that addition of a predetermined amount of ethanol will produce an ethanol-blended-product fuel qualified for end use.

17. The method of claim 7 wherein said first fuel is a sub-grade fuel, and said one or more fuel components include at least one fuel component the presence of which would substantially increase a risk of fuel contamination during transport in a fuel pipeline; and wherein said at least one fuel component is configured for addition to said first fuel at a point downstream of said fuel pipeline.

18. The method of claim 7 wherein said property comprises at least one of RON, MON, RVP, T(v/l)=20, specific gravity, aromatics, polynuclear aromatics, olefins, benzene, oxygen, ethanol, distillation, flash, viscosity, analine point, cetane number, and oxygenate percentage.

19. The method of claim 7 further comprising:
    determining property values of one or more intermediate-blended fuels that may be made by adding various amounts or identities of said one or more fuel components to said first fuel when making said second fuel from said first fuel.

20. The method of claim 19 further comprising determining if any of the one or more intermediate-blended fuels exhibits a property value that is beyond a threshold property value or property value range.

21. The method of claim 20 wherein said property value is a value of a property selected from a group of properties including RON, MON, RVP, T(v/l)=20, specific gravity, aromatics, polynuclear aromatics, olefins, benzene, oxygen, ethanol, distillation, flash, viscosity, analine point, cetane number, and oxygenate percentage.

22. The method of claim 7 wherein each of said first fuel and said second fuel is an intermediate fuel.

23. The method of claim 7 further comprising:
- determining property values of one or more intermediated-blended fuels that may be made by adding various amounts or identities of said one or more fuel components to said first fuel during a process of making said second fuel;
- wherein said first fuel is an intermediate fuel;
- wherein said second fuel is an alcohol-blended-product fuel qualified for end use; and
- wherein at least one of said one or more intermediate-blended fuels is a sub-grade fuel configured for transport from a refinery and further configured such that addition of a predetermined amount of ethanol will produce said alcohol-blended-product fuel.

24. A method for deriving a property value of a property of a refinery product, the method comprising:
- determining a property value of a first refinery product using a non-spectrographic test;
- determining a property value of the first refinery product using a first globally-calibrated spectrographic analyzer;
- determining a property value of a second refinery product using a second globally-calibrated spectrographic analyzer;
- wherein the property value of the second refinery product is determined by collecting spectral data for an intermediate fuel and constructing spectral data representative of the second refinery product by weighting the spectral data for the intermediate fuel together with spectral data for one or more other fuel components;
- determining a difference between the spectrographically-determined property values of the first refinery product and the second refinery product; and
- adding the difference to the non-spectrographically-determined property value of the first refinery product to derive a property value for the second refinery product.

25. The method of claim 24 wherein the refinery product comprises at least one of spark-ignited fuel, distillate fuel, and turbine fuel.

26. The method of claim 24 wherein the property comprises at least one of RON, MON, RVP, T(v/l)=20, specific gravity, aromatics, polynuclear aromatics, olefins, benzene, oxygen, ethanol, distillation, flash, viscosity, analine point, cetane number, and oxygenate percentage.

27. The method of claim 24 wherein the global calibration of the first and second globally-calibrated spectrographic analyzers is based on a plurality of location-specific and matrix-specific refinery product data.

* * * * *